(12) United States Patent
Ida et al.

(10) Patent No.: US 10,043,293 B2
(45) Date of Patent: Aug. 7, 2018

(54) IMAGE PROCESSING DEVICE, RADIATION DETECTING DEVICE, AND IMAGE PROCESSING METHOD

(71) Applicant: Toshiba Medical Systems Corporation, Otawara (JP)

(72) Inventors: Takashi Ida, Kawasaki (JP); Toshiyuki Ono, Kawasaki (JP); Shuhei Nitta, Ota (JP); Taichiro Shiodera, Shinagawa (JP); Hidenori Takeshima, Ebina (JP); Tomoyuki Takeguchi, Kawasaki (JP); Hiroaki Nakai, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 74 days.

(21) Appl. No.: 14/728,042

(22) Filed: Jun. 2, 2015

(65) Prior Publication Data
US 2015/0348289 A1    Dec. 3, 2015

(30) Foreign Application Priority Data

Jun. 3, 2014  (JP) .................... 2014-115110
Apr. 13, 2015 (JP) .................... 2015-081775

(51) Int. Cl.
*G06T 11/00*    (2006.01)
*A61B 6/00*    (2006.01)
*A61B 6/03*    (2006.01)

(52) U.S. Cl.
CPC ............ *G06T 11/005* (2013.01); *A61B 6/032* (2013.01); *A61B 6/481* (2013.01); *A61B 6/482* (2013.01); *A61B 6/5258* (2013.01)

(58) Field of Classification Search
CPC ... G06T 7/0012; G06T 7/0081; G06T 11/003; G06T 2207/10081; A61B 6/0306
See application file for complete search history.

(56) References Cited

U.S. PATENT DOCUMENTS

| | | | | |
|---|---|---|---|---|
| 4,577,222 A | * | 3/1986 | Kruger | A61B 6/02 378/22 |
| 5,289,126 A | * | 2/1994 | Mori | G01R 33/485 324/307 |

(Continued)

FOREIGN PATENT DOCUMENTS

| | | |
|---|---|---|
| JP | 6-181910 A | 7/1994 |
| JP | 2002-152495 A | 5/2002 |

(Continued)

*Primary Examiner* — Mia M Thomas
(74) *Attorney, Agent, or Firm* — Oblon, McClelland, Maier & Neustadt, L.L.P.

(57) ABSTRACT

An image processing device to reduce noise in a medical image includes first and second generators, a detector, and a corrector. A first image is generated based on data corresponding to photons with a first energy from among data that is obtained based on an energy of radiation that has passed through a subject and a second image is generated based on data corresponding to photons with a second energy. The detector finds, in the second image, a second block having a similar pattern of pixel values to a first block included in the second image. The corrector reduces noise by correcting pixel values of a third block in the first image corresponding to the first block based on new pixel values of the third block that are calculated by using pixel values included in a fourth block in the first image.

9 Claims, 19 Drawing Sheets

(56) References Cited

U.S. PATENT DOCUMENTS

| | | | |
|---|---|---|---|
| 6,898,332 B2 | 5/2005 | Matsuhira | |
| 7,492,947 B2* | 2/2009 | Nanbu | G06T 5/20 382/209 |
| 7,869,560 B2 | 1/2011 | Imai | |
| 7,974,451 B2* | 7/2011 | Matsumoto | G06T 3/00 128/922 |
| 7,974,473 B2 | 7/2011 | Nanbu | |
| 8,160,206 B2* | 4/2012 | Wu | A61B 6/032 378/4 |
| 8,260,023 B2* | 9/2012 | Thomsen | A61B 6/032 382/128 |
| 9,326,745 B2* | 5/2016 | Muraoka | A61B 6/5217 |
| 9,456,805 B2* | 10/2016 | Zalev | A61B 5/0095 |
| 2001/0043163 A1* | 11/2001 | Waldern | G02B 5/1885 345/7 |
| 2002/0136439 A1* | 9/2002 | Ruchala | A61B 6/08 382/131 |
| 2003/0194120 A1* | 10/2003 | Unger | A61B 6/405 382/132 |
| 2004/0044981 A1* | 3/2004 | Yoshimura | G03F 1/78 716/52 |
| 2004/0167387 A1* | 8/2004 | Wollenweber | A61B 6/037 600/407 |
| 2006/0093198 A1* | 5/2006 | Fram | A61B 6/463 382/128 |
| 2006/0098855 A1* | 5/2006 | Gkanatsios | A61B 5/0048 382/128 |
| 2006/0126889 A1* | 6/2006 | Nakamura | G06T 1/0064 382/100 |
| 2006/0140340 A1* | 6/2006 | Kravis | G01N 23/20 378/57 |
| 2006/0285747 A1* | 12/2006 | Blake | G06K 9/00234 382/180 |
| 2007/0036263 A1* | 2/2007 | Nishide | A61B 6/032 378/4 |
| 2007/0098133 A1* | 5/2007 | Chen | G06T 3/4076 378/4 |
| 2007/0110294 A1* | 5/2007 | Schaap | G06K 9/40 382/131 |
| 2007/0189443 A1* | 8/2007 | Walter | A61B 6/032 378/4 |
| 2007/0297562 A1* | 12/2007 | Konno | A61B 6/032 378/12 |
| 2008/0004517 A1* | 1/2008 | Bhandarkar | G06T 7/35 600/407 |
| 2008/0058593 A1* | 3/2008 | Gu | G06T 7/0012 600/109 |
| 2008/0058977 A1* | 3/2008 | Honda | G03F 1/86 700/110 |
| 2008/0239115 A1* | 10/2008 | Sugizaki | H04N 5/32 348/246 |
| 2009/0008581 A1* | 1/2009 | Fujiwara | A61B 6/025 250/580 |
| 2009/0080749 A1* | 3/2009 | Visser | G06T 5/50 382/131 |
| 2009/0147919 A1* | 6/2009 | Goto | A61B 6/032 378/86 |
| 2009/0160858 A1* | 6/2009 | Chen | G06T 17/005 345/424 |
| 2009/0190814 A1* | 7/2009 | Bouman | G06T 11/006 382/131 |
| 2009/0208074 A1* | 8/2009 | Wiersma | G06T 7/251 382/128 |
| 2010/0027743 A1* | 2/2010 | Engel | G01T 1/1647 378/62 |
| 2010/0166299 A1* | 7/2010 | Nobori | G06T 7/0071 382/162 |
| 2011/0116700 A1* | 5/2011 | Li | G01T 1/2985 382/131 |
| 2011/0118606 A1* | 5/2011 | Kim | G01S 15/8981 600/453 |
| 2011/0206258 A1* | 8/2011 | Chen | G06T 11/005 382/131 |
| 2011/0235780 A1* | 9/2011 | Tada | G01N 23/04 378/62 |
| 2011/0243302 A1* | 10/2011 | Murakoshi | G01N 23/04 378/62 |
| 2012/0148021 A1* | 6/2012 | Ishii | A61B 6/4233 378/62 |
| 2013/0083986 A1* | 4/2013 | Zeng | G06K 9/46 382/131 |
| 2013/0156267 A1* | 6/2013 | Muraoka | A61B 6/507 382/103 |
| 2013/0251229 A1* | 9/2013 | Ramirez Giraldo | G06T 11/003 382/131 |
| 2013/0287260 A1* | 10/2013 | Taguchi | G06T 11/003 382/103 |
| 2013/0343510 A1* | 12/2013 | Jang | G06T 7/0012 378/5 |
| 2014/0003704 A1* | 1/2014 | Liao | G06T 7/0075 382/154 |
| 2014/0018676 A1* | 1/2014 | Kong | A61B 5/015 600/438 |
| 2014/0036053 A1* | 2/2014 | Clingman | A61B 8/46 348/77 |
| 2014/0140601 A1* | 5/2014 | Litvin | G06T 11/005 382/131 |
| 2014/0185899 A1* | 7/2014 | Zalev | A61B 5/0095 382/131 |
| 2014/0193099 A1* | 7/2014 | Yoshikawa | A61B 8/5246 382/295 |
| 2015/0125059 A1* | 5/2015 | Holmes | A61B 6/032 382/131 |
| 2015/0243070 A1* | 8/2015 | Ra | A61B 6/503 382/131 |
| 2015/0379699 A1* | 12/2015 | Takeuchi | G01T 1/1647 348/77 |
| 2016/0000396 A1* | 1/2016 | Taguchi | A61B 6/5205 378/5 |

FOREIGN PATENT DOCUMENTS

| | | |
|---|---|---|
| JP | 2002-197455 A | 7/2002 |
| JP | 2007-87218 A | 4/2007 |
| JP | 2007-252653 A | 10/2007 |
| JP | 4170767 B2 | 10/2008 |
| JP | 2009-118887 A | 6/2009 |
| JP | 2013-119021 A | 6/2013 |
| WO | WO 02/086821 A1 | 10/2002 |
| WO | WO 2013/018575 A1 | 2/2013 |

* cited by examiner

IMAGE PROCESSING DEVICE, RADIATION DETECTING DEVICE, AND IMAGE PROCESSING METHOD

CROSS-REFERENCE TO RELATED APPLICATIONS

This application is based upon and claims the benefit of priority from Japanese Patent Application No. 2014-115110, filed on Jun. 3, 2014; and Japanese Patent Application No. 2015-081775, filed on Apr. 13, 2015, the entire contents of which are incorporated herein by reference.

FIELD

Embodiments described herein relate generally to image processing devices, radiation detecting devices, and image processing methods.

BACKGROUND

In recent years, the development of silicon-based photomultipliers is being actively pursued. Along with that, radiation detecting devices, such as X-ray computer tomography (CT) scanners, that include a photomultiplier are also being developed. In an X-ray CT scanner, X-rays that have passed through a subject are detected, and sectional images (reconstructed images) of the subject are reconstructed in which CT numbers (CT values) corresponding to the attenuation fraction of the X-rays are treated as pixel values. Herein, CT numbers (CT values) differ according to the substance through which the X-rays pass. Hence, by generating a reconstructed image, it becomes possible to observe the internal structure of the subject. However, if the radiation dose of X-rays is small, then the reconstructed image includes an increased number of pixels causing noise because of having CT numbers (CT values) with errors. As a result, observation of the subject becomes a difficult task.

In order to solve such an issue, a technique is known in which, aside from a normal reconstructed image, a blurred reconstructed image is also generated in which noise does not occur easily. Then, the blurred reconstructed image is used in detecting the directions of edges of the substances; and smoothing in the detected directions of edges is performed with respect to the normal reconstructed image. With that, an image is obtained in which noise is reduced without causing defocussing of the edges. However, in such a smoothing operation, a simple mean filter or a weighted mean filter is used. Hence, although it is possible to reduce the spatial high-frequency components of the noise representing local irregularity, it is not possible to reduce the low-frequency components. For that reason, there remains unevenness in the image, and the accuracy of CT numbers (CT values) is not enhanced.

DETAILED DESCRIPTION

Figure 1:
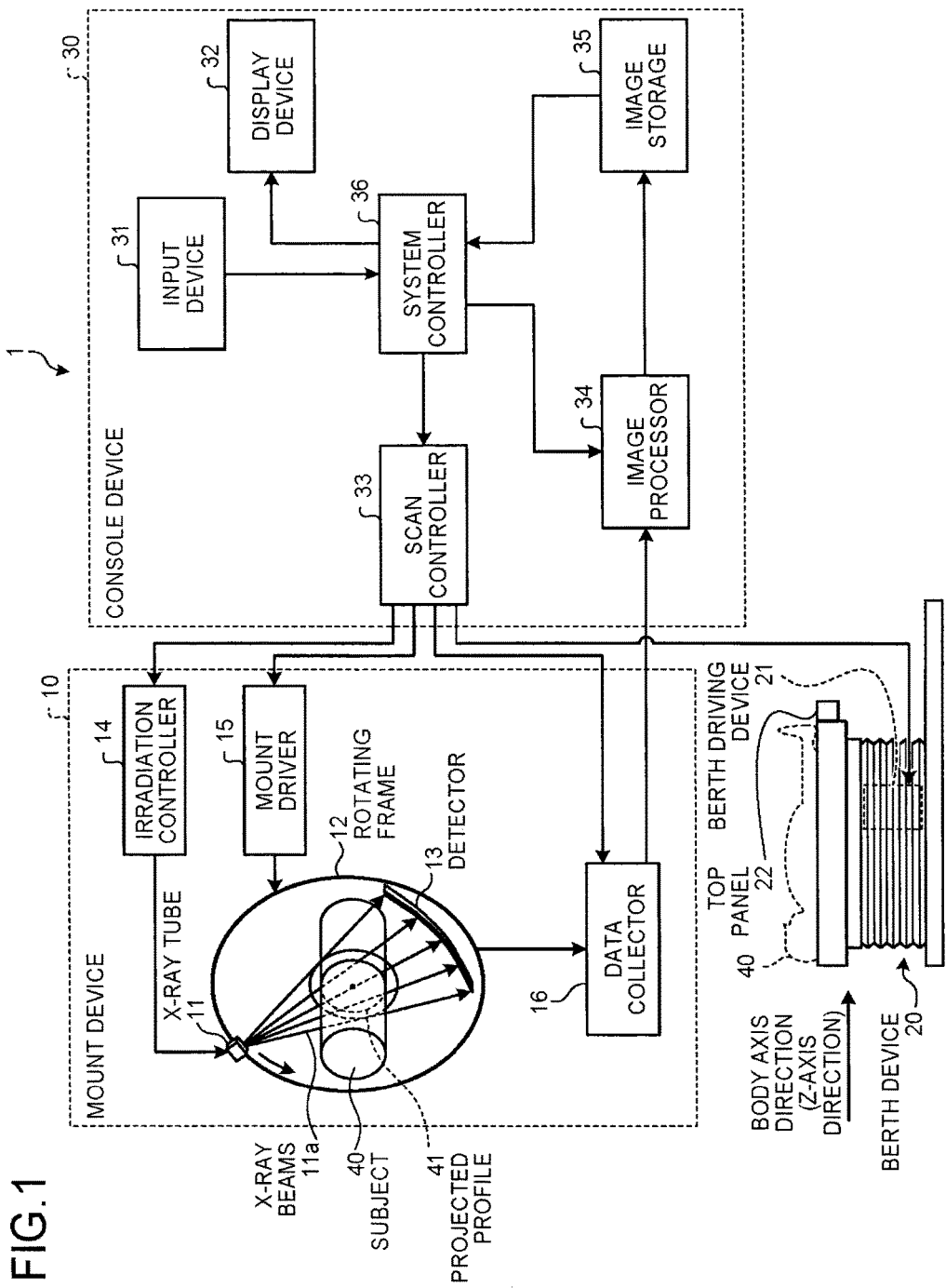
FIG. 1 is a diagram illustrating an overall configuration of an X-ray inspection device according to a first embodiment.

According to an embodiment, an image processing device includes a first generator, a second generator, a detector, and a corrector. The first generator is configured to generate a first image based on first data corresponding to photons with a first energy from among data that is obtained based on an energy of radiation that has passed through a subject bombarded with the radiation. The second generator is configured to generate a second image based on second data corresponding to photons with a second energy different from the first energy. The detector is configured to detect, in the second image, a second block having a similar pattern of pixel values to a first block included in the second image. The corrector is configured to calculate, by using pixel values included in a third block in the first image that is positioned corresponding to position of the first block in the second image and pixel values included in a fourth block in the first image that is positioned corresponding to position of the second block in the second image, new pixel values of the third block, and perform a correction on pixel values of the third block based on the new pixel values of the third block.

Exemplary embodiments of an image processing device, a radiation detecting device, and an image processing method according to the invention are described below in detail with reference to the accompanying drawings. In the accompanying drawings, the same constituent elements are referred to by the same reference numerals. However, the drawings are only schematic in nature, and the specific configuration should be determined by taking into account the explanation given below.

First Embodiment

FIG. 1 is a diagram illustrating an overall configuration of an X-ray inspection device according to a first embodiment. Thus, the brief outline of the overall configuration of the X-ray inspection device is given with reference to FIG. 1.

As illustrated in FIG. 1, an X-ray inspection device 1, which is an example of a radiation detecting device, is a spectral CT scanner or a photon counting CT scanner in which X-rays, which are an example of radiation, are passed through a subject 40 and are detected as a spectrum represented by an energy-by-energy photon count; and an image of a projected profile 41 of the subject 40 is obtained. As illustrated in FIG. 1, the X-ray inspection device 1 includes a mount device 10, a berth device 20, and a console device 30.

The mount device 10 is a device that bombards the subject 40 with X-rays so that the X-rays pass through the subject 40, and detects the spectrum mentioned above. The mount device 10 includes an X-ray tube 11 (an example of a radiation tube), a rotating frame 12, a detector 13, an irradiation controller 14, a mount driver 15, and a data collector 16.

The X-ray tube 11 is a vacuum tube for generating X-rays in response to a high voltage supplied from the irradiation controller 14, and bombarding the subject 40 with X-ray beams 11a. The spectrum represented by the energy-by-energy photon count of the X-rays, which are emitted from the X-ray tube 11, is determined according to the tube voltage of the X-ray tube 11, the tube current of the X-ray tube 11, and the type of target used in the radiation source (for example, tungsten is used). When the X-rays emitted from the X-ray tube 11 pass through the subject 40, according to the condition of the substances constituting the subject 40, the photon count of each energy decreases and the spectrum undergoes a change.

The rotating frame 12 is a ring-shaped supporting member that supports the X-ray tube 11 and the detector 13 in such a way that the X-ray tube 11 and the detector 13 are positioned opposite to each other across the subject 40.

The detector 13 detects, on a channel-by-channel basis, the energy-by-energy photon count of the X-rays that have been emitted from the X-ray tube 11 and that have passed through the subject 40. As illustrated in FIG. 1, the detector 13 detects the spectrum on a view-by-view basis while rotating in the circumferential direction of the rotating frame 12. Herein, views represent predetermined angles at which the detector 13 detects the spectrum in 360° of the circumference in the circumferential direction of the rotating frame 12. That is, if the detector 13 detects the spectrum after every 2°, then a single view is equal to 2°. Meanwhile, the detector 13 is a two-dimensional array type detector in which a plurality of detecting element arrays, each having a plurality of detecting elements arranged in a channel direction (the circumferential direction of the rotating frame 12), is arranged along the body axis direction of the subject 40 (along the Z-axis direction illustrated in FIG. 1).

The irradiation controller 14 is a device that generates a high voltage and supplies it to the X-ray tube 11.

The mount driver 15 is a processing unit that rotary-drives the rotating frame 12, and consequently rotary-drives the X-ray tube 11 and the detector 13 on a circular path around the subject 40.

The data collector 16 is a device that collects data of the spectrum which is detected on a channel-by-channel basis by the detector 13 and which is represented by the energy-by-energy photon count. Moreover, the data collector 16 performs amplification and A/D conversion with respect to each set of collected data, and outputs the processed data to the console device 30.

The berth device 20 is a device on which the subject 40 is made to lie down and, as illustrated in FIG. 1, includes a berth driving device 21 and a top panel 22.

The top panel 22 is a panel on which the subject 40 is made to lie down. The berth driving device 21 is a device that moves the top panel 22 in the body axis direction of the subject 40 (the Z-axis direction) so that the subject 40 moves inside the rotating frame 12.

The console device 30 is a device that receives an operation performed by an operator with respect to the X-ray inspection device 1, and reconstructs a cross-sectional image from the data collected by the mount device 10. As illustrated in FIG. 1, the console device 30 includes an input device 31, a display device 32, a scan controller 33, an image processor 34, an image storage 35, and a system controller 36.

The input device 31 is a device operated by the operator of the X-ray inspection device 1 to input various instructions, and sends the various input commands to the system controller 36. The input device 31 is implemented using, for example, a mouse, a keyboard, buttons, a trackball, or a joystick.

The display device 32 is a device for displaying a graphical user interface (GUI), which is used in receiving instructions from the operator via the input device 31, and displaying reconstructed images stored in the image storage 35 (described later). The display device 32 is implemented using, for example, a cathode ray tube (CRT) display, a liquid crystal display (LCD), or an organic electro-luminescence (EL) display.

The scan controller 33 controls the operations of the irradiation controller 14, the mount driver 15, the data collector 16, and the berth driving device 21. More particularly, the scan controller 33 performs X-ray scanning by making the X-ray tube 11 emit X-rays in a continuous or intermittent manner while rotating the rotating frame 12. For example, the scan controller 33 performs helical scanning in which images are captured by continuously rotating the rotating frame 12 while moving the top panel 22; or performs non-helical scanning in which, firstly, images are captured by rotating the rotating frame 12 for one revolution. Then, the top panel 22 on which the subject 40 is made to lie down is shifted slightly and images are captured again by rotating the rotating frame 12 for one revolution.

The image processor 34 is a processing unit that generates a sinogram based on the spectrum data collected by the data collector 16, and reconstructs a tomographic image of the subject 40 from the sinogram. Regarding a block configuration and the operations of the image processor 34, the details are given later.

The image storage 35 is used to store the tomographic image (a restored image) generated during a reconstruction process performed by the image processor 34. The image storage 35 is implemented using a memory medium such as a hard disk drive (HDD), a solid state drive (SSD), or an optical disk.

The system controller 36 controls the entire X-ray inspection device 1 by controlling the operations of the mount device 10, the berth device 20, and the console device 30. More particularly, the system controller 36 controls the scan controller 33 so as to control the operation of collecting the spectrum data of the subject 40 performed by the mount device 10 and the berth device 20. Moreover, the system controller 36 controls the image processor 34 so as to control the reconstruction process for generating a tomographic image. Furthermore, the system controller 36 reads the tomographic image from the image storage 35, and displays it on the display device 32.

Figure 2:
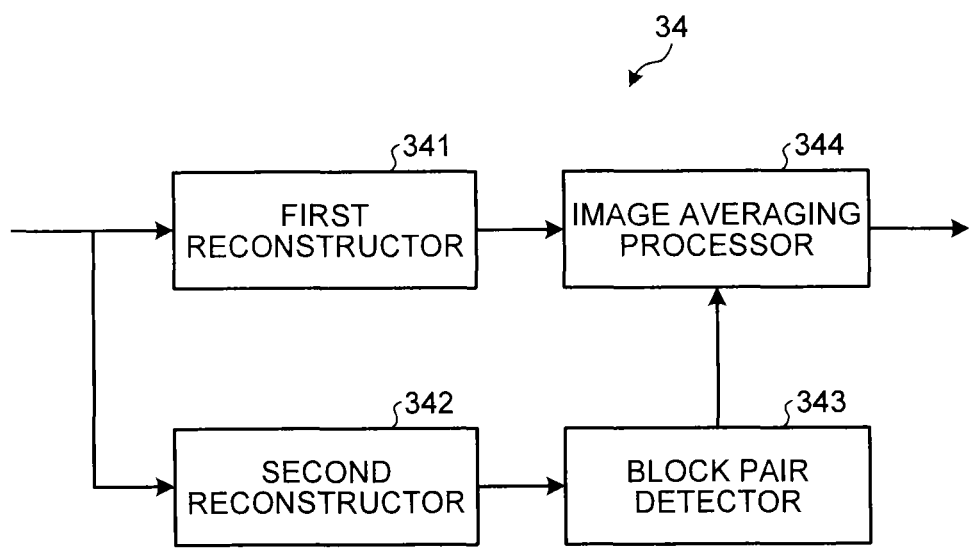
FIG. 2 is a block configuration diagram of an image processor according to the first embodiment.
Figure 3:
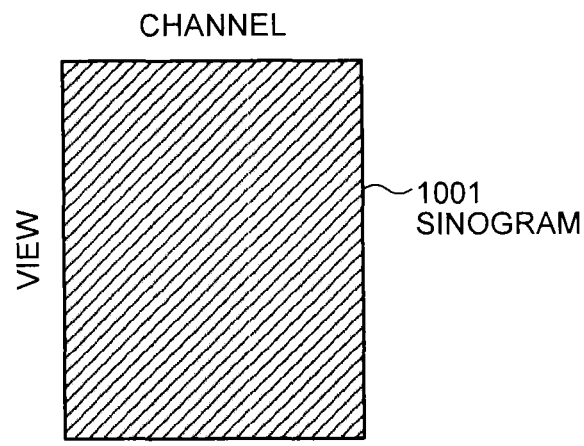
FIG. 3 is a diagram for explaining a sinogram.
Figure 4:
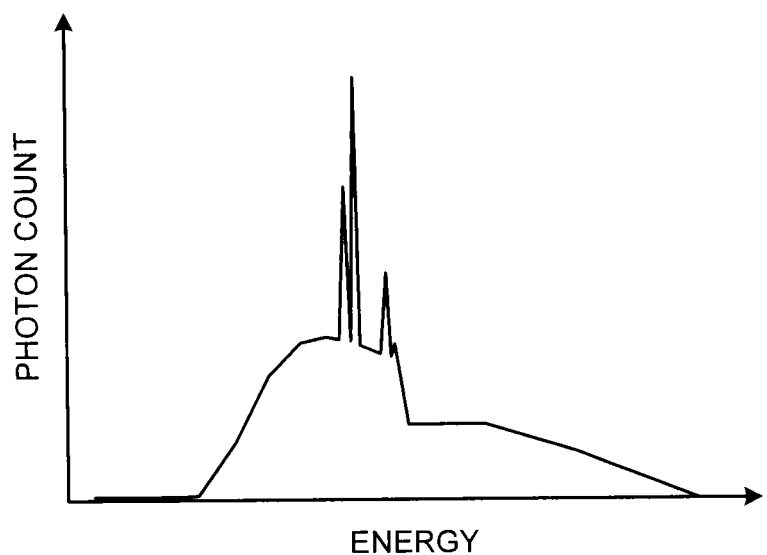
FIG. 4 is a diagram illustrating an exemplary energy spectrum detected in a specific channel of a detector.
Figure 5:
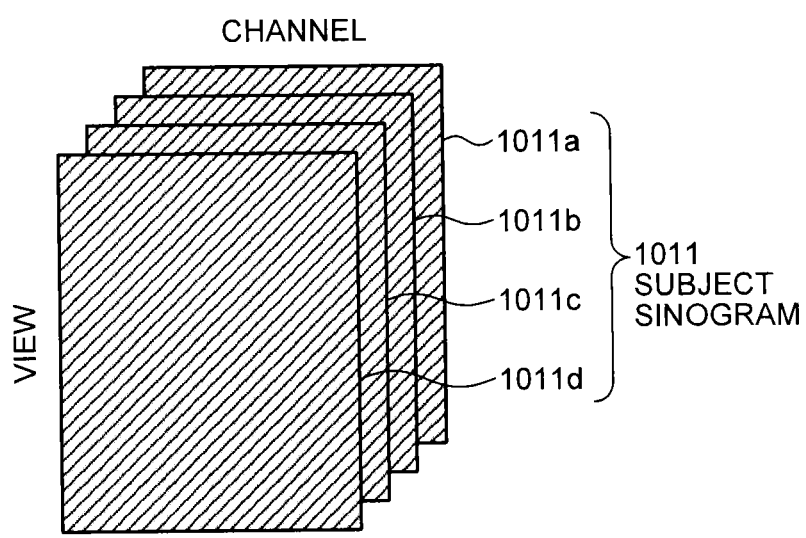
FIG. 5 is a diagram illustrating an example of a subject sinogram.
Figure 6:
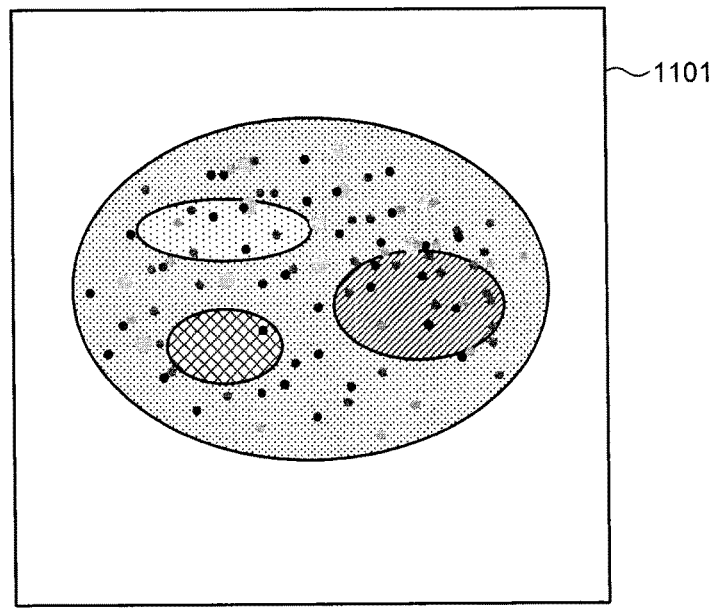
FIG. 6 is a diagram illustrating an exemplary reconstructed image that is reconstructed with photons of a specific energy.
Figure 7:
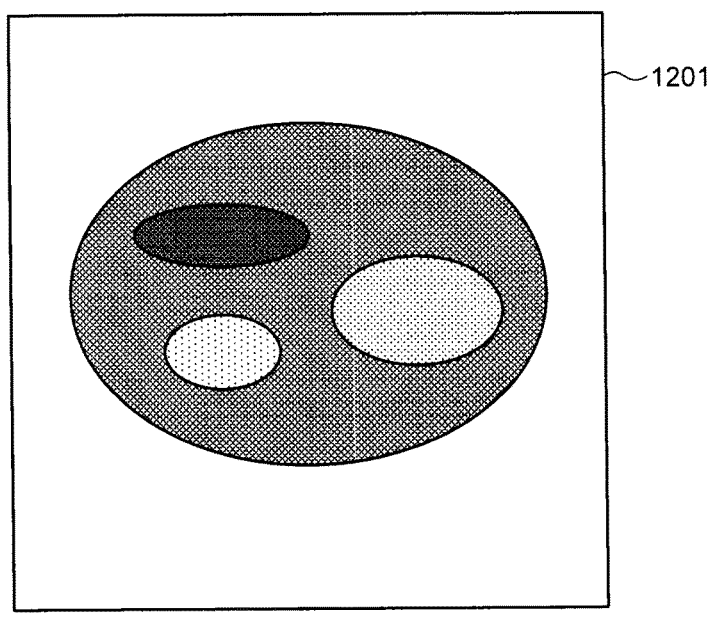
FIG. 7 is a diagram illustrating an exemplary reconstructed image that is reconstructed with photons of a plurality of energies.

FIG. 2 is a block configuration diagram of the image processor according to the first embodiment. FIG. 3 is a diagram for explaining a sinogram. FIG. 4 is a diagram illustrating an exemplary energy spectrum detected in a specific channel of the detector. FIG. 5 is a diagram illustrating an example of a subject sinogram. FIG. 6 is a diagram illustrating an exemplary reconstructed image that is reconstructed with photons of a specific energy. FIG. 7 is a diagram illustrating an exemplary reconstructed image that is reconstructed with photons of a plurality of energies or with all energies. Thus, explained below with reference to FIGS. 2 to 6 is the brief outline of a configuration and the operations of the image processor 34 according to the first embodiment.

As illustrated in FIG. 2, the image processor 34 includes a first reconstructor 341 (a first generator), a second reconstructor 342 (a second generator), a block pair detector 343 (a detector), and an image averaging processor 344 (a corrector).

The first reconstructor 341 is a processing unit that generates a subject sinogram (described later) from the spectrum represented by the energy-by-energy photon count of the X-rays; generates an attenuation sinogram (a first sinogram) (described later) based on the test sinogram; and generates a reconstructed image by reconstructing the attenuation sinogram. Herein, as in the case of a sinogram 1001 illustrated in FIG. 3, a sinogram is an image in which, for each view of the X-ray tube 11, the channel-by-channel measured values detected by the detector 13 are arranged as pixel values. A sinogram generated from the spectrum detected by the detector 13 when the X-rays emitted from the X-ray tube 11 pass through the subject 40 is called a subject sinogram. Moreover, a sinogram generated from the spectrum detected by the detector 13 when the subject 40 is not present and the X-rays pass only through the air is called an air sinogram. In a subject sinogram and an air sinogram, a pixel value represents a photon count detected as a measured value by the detector 13. Moreover, the detector 13 detects, for each view and for each channel, a spectrum represented by the energy-by-energy photon count. Therefore, as a result of performing X-ray scanning for one revolution of the X-ray tube 11, it becomes possible to obtain an energy-by-energy subject sinogram 1011 as illustrated in FIG. 5. In the example illustrated in FIG. 5, the spectrum is divided into four energy bands, and four subject sinograms 1011a to 1011d are obtained for the four energy bands (hereinafter, simply referred to as "energies"). Although it is illustrated in the example in FIG. 5 that the spectrum is divided into four energy bands, the number of divisions is not limited to four.

The first reconstructor 341 receives data of the spectrum (see FIG. 4) which is detected on a channel-by-channel basis by the detector 13, which is represented by the energy-by-energy photon count of the X-rays that have passed through the subject 40, and which is collected by the data collector 16. Then, from the received spectrum, the first reconstructor 341 generates a subject sinogram of a specific energy of the desired type (the energy of interest) (a first energy); and generates an attenuation fraction sinogram based on the subject sinogram. Herein, the "specific energy" does not exclusively imply the energy having a specific single value. Rather, the "specific energy" represents the idea of including a specific energy band. That idea is followed in the following explanation too.

More particularly, the first reconstructor 341 calculates, in the subject sinogram, the attenuation fraction for each view and for each channel; and generates an attenuation fraction sinogram in which the attenuation fractions serve as pixel values. As far as the method of calculating the attenuation fractions is concerned, if the photon count of the X-rays emitted from the X-ray tube 11 is known, then the attenuation fraction for each view and for each channel is calculated as follows: attenuation fraction=(the photon count emitted in the concerned channel and the concerned view from the X-ray tube 11)/(the photon count detected in the concerned channel and the concerned view by the detector 13 after the passage of photons through the subject 40). On the other hand, if the photon count of the X-rays emitted from the X-ray tube 11 is not known, then the first reconstructor 341 receives input of the spectrum detected by the detector 13 when the subject 40 is not present and generates an air sinogram from that spectrum. Then, the attenuation fraction for each view and for each channel is calculated as follows: attenuation fraction=(the photon count (the pixel values) in the air sinogram)/(the photon count (the pixel values) in the subject sinogram).

Subsequently, the first reconstructor 341 implements a known technology such as the back projection method or the successive approximation to reconstruct the generated attenuation sinogram and, as illustrated in FIG. 6, generates a reconstructed image 1101 (a first image) having linear attenuation coefficients as pixel values. Then, the first reconstructor 341 sends the reconstructed image 1101 to the image averaging processor 344. Meanwhile, the linear attenuation coefficients differ according to the type and the concentration of the substance through which the X-rays are passed. Hence, if the distribution of linear attenuation coefficients is made visible in a reconstructed image, then it enables recognition of the internal structure of the subject 40. Moreover, the linear attenuation coefficients differ also according to the energies of the photons of X-rays. Hence, if a particular substance is to be observed, then the spectrum of an energy for which the difference in linear attenuation coefficients with other substances is large can be used to enhance the contrast between substances. As a result, it becomes possible to obtain a reconstructed image having a high degree of visibility.

In the back projection method, firstly, the measured values detected by the detector 13 in a particular view are written in the entire image to be reconstructed; and that operation is performed in all views. In that case, since the values remain also in the positions where the subject 40 is not present, a blurred image is obtained. However, if filter processing is performed using a filter that reinforces the edges and reduces the artifact, then the edges are reinforced thereby cancelling out the blurring. As a result, a clear reconstructed image is obtained. Regarding the method of performing filter processing, a method can be implemented in which Fourier transform is performed followed by filter processing in a frequency domain, or a method can be implemented in which filter processing is performed in the real space according to convolution. The method for correcting reconstructed images using a filter is particularly called the filtered back projection (FBP) method.

Meanwhile, in the successive approximation, a provisional image is provided in advance in a pseudo manner, and the attenuation fraction in each view is calculated when the subject is bombarded with X-rays. If the attenuation fractions calculated in the provisional image are smaller than the measured values (the attenuation fractions) that are actually detected by the detector 13, then the pixel values in the provisional image are increased. On the other hand, if the attenuation fractions calculated in the provisional image are greater than the measured values that are actually detected by the detector 13, then the pixel values in the provisional image are reduced. Such operations are performed in a repeated manner so that the attenuation fractions calculated in the provisional image are changed to be equal to the measured values (the attenuation fractions) that are actually detected by the detector 13; and a reconstructed image is obtained. Examples of the successive approximation include the OS-EM method (OS-EM stands for Ordered Subset Expectation Maximization) and the ML-EM method (ML-EM stands for Maximum Likelihood Expectation Maximization).

As described above, the first reconstructor 341 generates a subject sinogram of a specific energy of the desired type from the spectrum represented by the energy-by-energy photon count of the X-rays. However, the photon count, which serves as the pixel value constituting the subject sinogram, is small. For that reason, the quantum fluctuation or the detector error has a significant impact. Hence, as illustrated in FIG. 6, the linear attenuation coefficients, which serve as the pixel values of the reconstructed image 1101, include errors and exhibit high variability. Therefore, the linear attenuation coefficients become values of low accuracy.

The second reconstructor 342 is a processing unit that generates, from the spectrum represented by the energy-by-energy photon count of the X-rays, a subject sinogram (a second sinogram) in which the photon counts of a plurality of energies or the photon counts of all energies of the spectrum are added for each view and for each channel; and reconstructs the subject sinogram to generate a reconstructed image 1201 as illustrated in FIG. 7.

Firstly, the second reconstructor 342 receives input of data of the spectrum (see FIG. 4) which is detected on a channel-by-channel basis by the detector 13, which is represented by the energy-by-energy photon count of the X-rays that have passed through the subject 40, and which is collected by the data collector 16. Then, the second reconstructor 342 generates, from the received spectrum, a subject sinogram (second data) of either a plurality of energies of the spectrum or all energies of the spectrum (a second energy). The second reconstructor 342 implements the back projection method or the successive approximation to reconstruct the subject sinogram and generates the reconstructed image 1201 (a second image). Then, the second reconstructor 342 sends the reconstructed image 1201 to the block pair detector 343. In the subject sinogram generated by the second reconstructor 342, the pixel values represent values obtained by adding the photon counts of a plurality of energies of the spectrum or the photon counts of all energies of the spectrum. Thus, in the reconstructed image 1201 that is reconstructed from the subject sinogram, the pixel values have less variability as compared to the reconstructed image 1101 generated by the first reconstructor 341, but are different than the linear attenuation coefficients at a specific energy.

The block pair detector 343 is a processing unit that divides the reconstructed image 1201, which is received from the second reconstructor 342, into child blocks and detects parent blocks each of which has a similar pattern of pixel values to one of the child blocks (in the following explanation "similar pattern of pixel values" is sometimes simply referred to as "similar"). Then, the block pair detector 343 sends position information about pairs of child blocks and the respective similar parent blocks (hereinafter, called block pairs) to the image averaging processor 344. Regarding the operations performed by the block pair detector 343, the details are given later. Moreover, although explained later during the description of the operations performed by the block pair detector 343, "similar" is a concept not only implying a case in which the patterns of pixel values in two blocks are completely similar to each other, but also implying a case in which the patterns of pixel values in two blocks may include a predetermined error in similarity.

The image averaging processor 344 is a processing unit that, in the reconstructed image 1101 received from the first reconstructor 341, arranges the block pairs at the positions indicated by the position information of block pairs that is received from the block pair detector 343; and performs an averaging process in which the pixel values are replaced with values that are obtained by performing weighted averaging of the pixel values of the child blocks and the pixel values of reduced blocks obtained by reducing the parent blocks. Regarding the operations performed by the image averaging processor 344, the details are given later.

Meanwhile, the first reconstructor 341, the second reconstructor 342, the block pair detector 343, and the image averaging processor 344 included in the image processor 34 can be implemented using software such as computer programs or can be implemented using hardware circuitry. Moreover, the first reconstructor 341, the second reconstructor 342, the block pair detector 343, and the image averaging processor 344 included in the image processor 34 illustrated in FIG. 2 represent only a conceptual illustration of the functions, and the configuration is not limited to that example.

In the first embodiment, the console device 30 has the configuration of a commonly-used computer. That is, the console device 30 includes a control device such as a central processing unit (CPU) (the scan controller 33 and the system controller 36 illustrated in FIG. 1), a memory device such as a read only memory (ROM) or a random access memory (RAM), an external memory device such as a hard disk drive (HDD) or a CD drive (the image storage 35 illustrated in FIG. 1), and a display device such as a display (the display device 32 illustrated in FIG. 1). As described above, if at least one of the first reconstructor 341, the second reconstructor 342, the block pair detector 343, and the image averaging processor 344 included in the image processor 34 is implemented using computer programs; then the computer programs executed in the console device 30 are recorded as installable or executable files in a computer-readable recording medium such as a compact disk read only memory (CD-ROM), a flexible disk (FD), a compact disk readable (CD-R), or a digital versatile disk (DVD). Alternatively, the computer programs executed in the console device 30 can be saved as downloadable files on a computer connected to the Internet or can be made available for distribution through a network such as the Internet. Still alternatively, the computer programs can be stored in advance in a ROM or the like. Meanwhile, the computer programs executed in the console device 30 according to the first embodiment contain a module for at least one of the first reconstructor 341, the second reconstructor 342, the block pair detector 343, and the image averaging processor 344 included in the image processor 34. As the actual hardware, a CPU reads the computer programs from the recording medium and executes them so that the computer programs are loaded in a main memory device and the constituent elements are generated in the main memory device. These details are also applicable to the modification examples and other embodiments described below.

Figure 8:
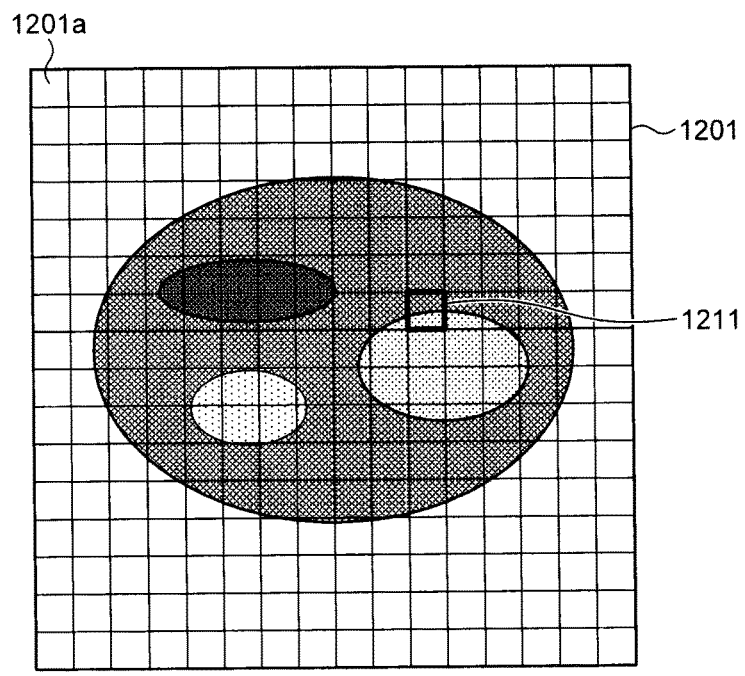
FIG. 8 is a diagram illustrating a state in which a reconstructed image is divided into child blocks.
Figure 9:
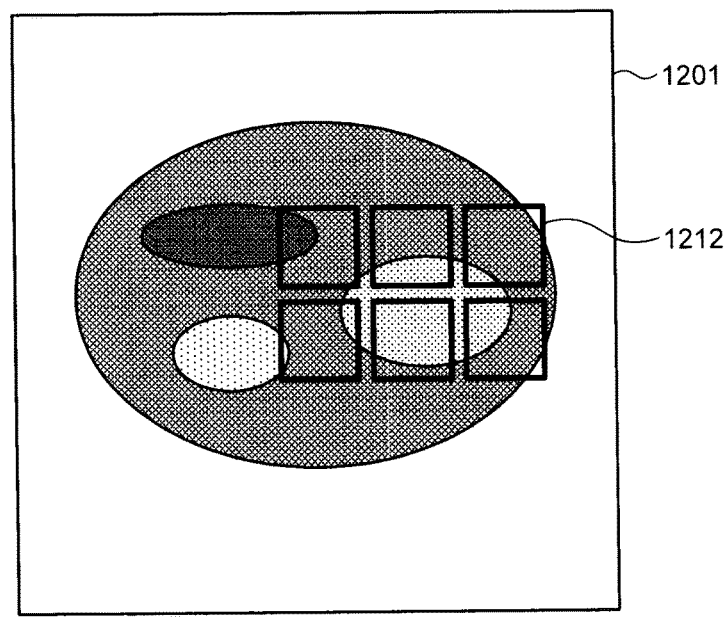
FIG. 9 is a diagram illustrating exemplary parent blocks set around a target child block.
Figure 10:
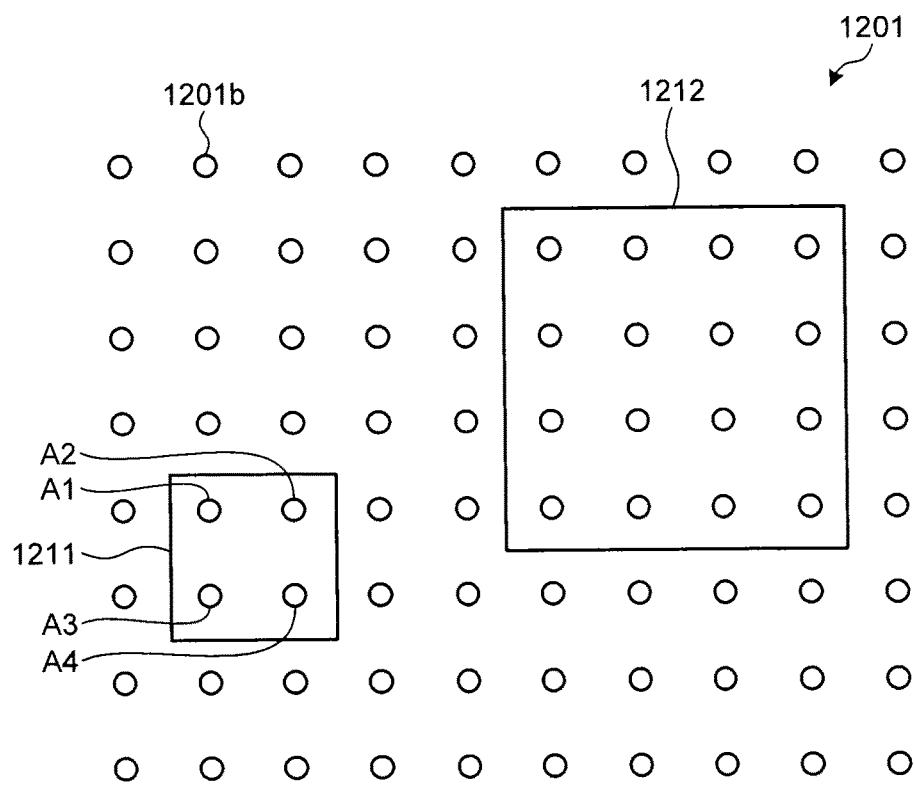
FIG. 10 is a diagram illustrating exemplary parent blocks which are targets for comparison with a target child block.
Figure 11:
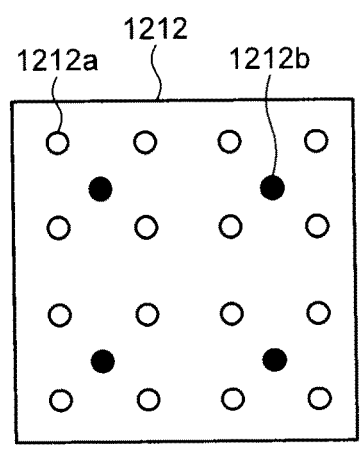
FIG. 11 is a diagram for explaining the creation of a reduced block from a parent block.
Figure 12:
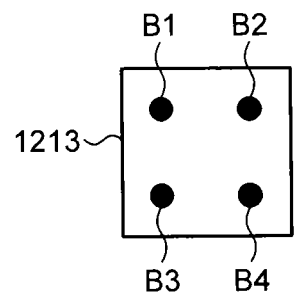
FIG. 12 is a diagram illustrating an exemplary reduced block that is created.
Figure 13:
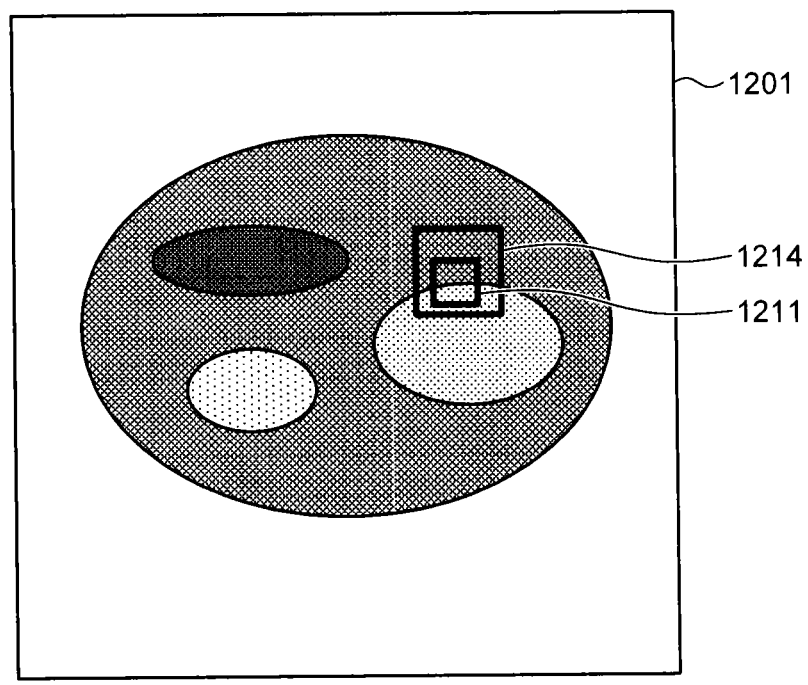
FIG. 13 is a diagram illustrating an example in which a parent block similar to a child block is detected.
Figure 14:
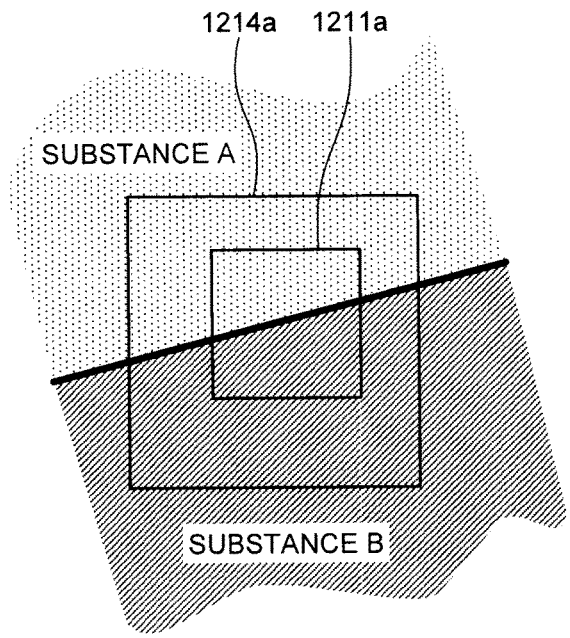
FIGS. 14 to 16 are diagrams illustrating examples of block pairs.
Figure 15:
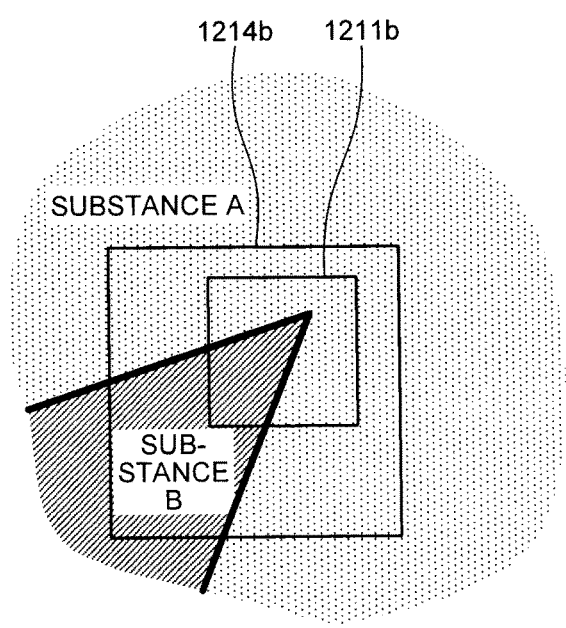
Figure 16:
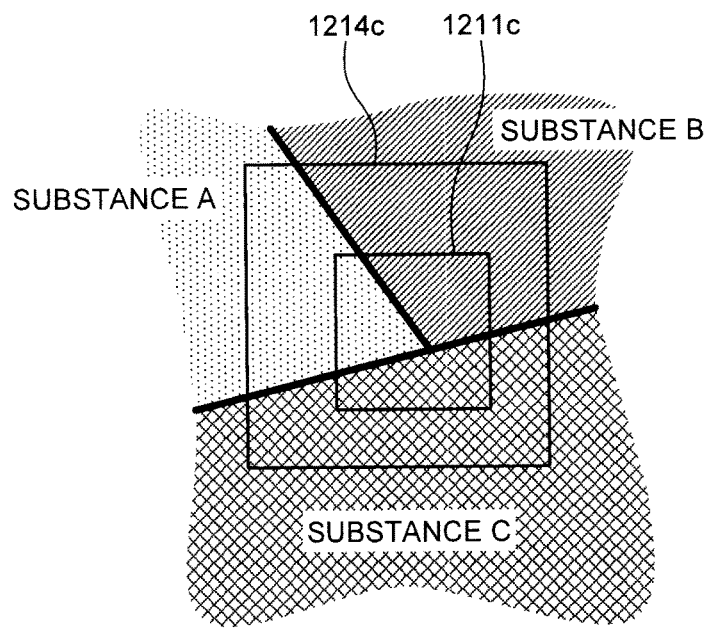

FIG. 8 is a diagram illustrating the state in which a reconstructed image is divided into child blocks. FIG. 9 is a diagram illustrating exemplary parent blocks set around a target child block. FIG. 10 is a diagram illustrating exemplary parent blocks which are targets for comparison with a target child block. FIG. 11 is a diagram for explaining the creation of a reduced block from a parent block. FIG. 12 is a diagram illustrating an exemplary reduced block that is created. FIG. 13 is a diagram illustrating an example in which a parent block similar to a child block is detected. FIGS. 14 to 16 are diagrams illustrating examples of block pairs. Thus, explained below with reference to FIGS. 8 to 16 are the operations performed by the block pair detector 343 of the image processor 34 according to the first embodiment.

As described above, the reconstructed image 1201, which is generated as illustrated in FIG. 7 by the second reconstructor 342, has less variability in the pixel values. In FIG. 7, substances having different pixel values are represented as ellipses. The block pair detector 343 divides the reconstructed image 1201 illustrated in FIG. 7 into areas (hereinafter, called child blocks) (first blocks) segmented in a reticular pattern. In FIG. 8 is illustrated an example in which the reconstructed image 1201 is divided into child blocks 1201a segmented in a reticular pattern.

Then, for each target child block 1211 that is the target child block for processing from among the divided child blocks 1201a, the block pair detector 343 searches for a parent block 1212 (a second block) that is larger than the concerned child block and that has a similar pattern of pixel values. Herein, as illustrated in FIG. 9, a plurality of parent blocks 1212 is set in a predetermined area around the target child block 1211, and the parent blocks 1212 are searched for the parent block 1212 having a similar pattern of pixel values to the target child block 1211. Alternatively, in a predetermined area around the target child block 1211, the block pair detector 343 shifts the parent block 1212 having the concerned size one pixel at a time and searches for the parent block 1212 having a similar pattern of pixel values to the target child block 1211.

Given below is the detailed explanation of the method by which the block pair detector 343 searches for the parent block 1212 having a similar pattern of pixel values to the target child block 1211. As illustrated in FIG. 10, the reconstructed image 1201 is assumed to be made of pixels 1201b, and the target child block 1211 is assumed to be made of, for example, 2×2 pixels (pixels A1 to A4). Moreover, as illustrated in FIG. 10, for example, the parent block 1212 that is a parent block candidate having a similar pattern of pixel values to the target child block 1211 is assumed to be made of 4×4 pixels. With respect to the parent block 1212 illustrated in FIG. 10, the block pair detector 343 uses the pixel value of pixels 1212a in the parent block 1212 illustrated in FIG. 11 and performs a reduction process by implementing a bilinear method in which the pixel values of four surrounding pixels are averaged at positions 1212b illustrated as filled circles, or by implementing the nearest neighbor method, or by implementing the cubic convolution interpolation. As a result of performing the reduction process, as illustrated in FIG. 12, the block pair detector 343 generates a reduced block 1213 made of pixels B1 to B4 and having the same size as the target child block 1211.

Subsequently, using pixel values $a1a$ to $a4a$ of the pixels A1 to A4, respectively, of the target child block 1211 and using pixel values $b1a$ to $b4a$ of the pixels B1 to B4, respectively, of the reduced block 1213, the block pair detector 343 calculates an absolute value error using, for example, Equation (1) given below.

$$\text{(absolute value error)} = |a1a - b1a| + |a2a - b2a| + |a3a - b3a| + |a4a - b4a| \quad (1)$$

The block pair detector 343 determines that, of a plurality of parent blocks 1212, the parent block 1212 corresponding to the reduced block 1213 having the smallest absolute value error is similar to the target child block 1211, and detects that particular parent block 1212 as a detected parent block 1214 illustrated in FIG. 13. In this way, for each child block 1201a constituting the reconstructed image 1201, the block pair detector 343 searches for the parent block having a similar pattern of pixel values and detects that particular parent block as the detected parent block. Moreover, regarding the parent block 1212 corresponding to the reduced block 1213 having the smallest absolute value error, if the absolute value error is not equal to or smaller than a threshold value, then the block pair detector 343 determines that the target child block 1211 does not have any similar parent block 1212, and thus does not perform subsequent operations. As a result, it becomes possible to avoid unnecessary operations.

Herein, although the block pair detector 343 calculates the absolute value error between the target child block 1211 and the reduced block 1213, that is not the only possible case. Alternatively, for example, using the pixel values $a1a$ to $a4a$ of the target child block 1211 and using the pixel values $b1a$ to $b4a$ of the reduced block 1213, the block pair detector 343 can calculate a squared error as given below in Equation (2). Then, the block pair detector 343 can determine that, of a plurality of parent blocks 1212, the parent block 1212 corresponding to the reduced block 1213 having the smallest squared error is similar to the target child block 1211 and detects that particular parent block 1212 as the detected parent block 1214.

$$\text{(squared error)} = (a1a - b1a)^2 + (a2a - b2a)^2 + (a3a - b3a)^2 + (a4a - b4a)^2 \quad (2)$$

Meanwhile, as illustrated in FIG. 10, the target child block 1211 is assumed to be made of 2×2 pixels and the parent block 1212 is assumed to be made of 4×4 pixels. However, that is only exemplary. Alternatively, the target child block 1211 and the parent block 1212 can have other different sizes.

Moreover, as described above, the block pair detector 343 performs a reduction process with respect to the parent block 1212 and generates the reduced block 1213. However, that is not the only possible case. Alternatively, the block pair detector 343 can expand the target child block 1211 to the same size of the parent block 1212, and can determine whether or not the target child block 1211 and the parent block 1212 are similar to each other using the error (for example, the absolute value error or the squared error) between the expanded block and the parent block 1212.

Furthermore, as described above, in order to determine whether or not the target child block 1211 and the parent block 1212 are similar to each other, the block pair detector 343 makes use of the absolute value error or the squared error. However, the error is not limited to such types. Alternatively, for example, other types of error, such as the average absolute value error or the error of mean square, can also be used as the error.

In FIG. 13 is illustrated a pair (hereinafter, called a block pair) of the target child block 1211 and the detected parent block 1214, which is determined by the block pair detector 343 to be similar to the target child block 1211. Meanwhile, in FIG. 13, for comparison with the reconstructed image 1101 illustrated in FIG. 6, the reconstructed image 1201 is illustrated to be a simplified image having no pixel variability. However, in reality, there is some variability in the pixel values even if the pixel count is large, and sometimes the degree of contrast among substances also varies. In such a case too, according to the method described above, it is possible to detect the parent block (the detected parent block) having a similar pattern to the original pattern of a substance (the pattern of pixel values).

In FIGS. 14 to 16 are illustrated examples of block pairs. As in the case of the block pair illustrated in FIG. 14 (a pair of a target child block 1211a and a detected parent block 1214a), if the boundary between a substance A and a substance B is a straight line, then it is possible to detect a parent block that is completely similar to a child block including the boundary. Moreover, as in the case of the block pair illustrated in FIG. 15 (a pair of a target child block 1211b and a detected parent block 1214b), if the boundary between the substance A and the substance B is a corner-shaped boundary, then it is possible to detect a parent block that is completely similar to a child block including the corner-shaped boundary. Furthermore, as in the case of the block pair illustrated in FIG. 16 (a pair of a target child block 1211c and a detected parent block 1214c), if the boundaries between substances A to C are straight lines, then it is possible to detect a parent block that is completely similar to a child block formed across the substances A to C. Meanwhile, if the boundary between substances is a curved line, a similar block pair is not detected in a precise sense. However, if the size of the blocks is reduced, then the boundary locally becomes a straight line, and an almost similar block pair can be detected. Regarding a child block and a parent block that are mutually similar, if the parent block is reduced or if the child block is expanded so as to match the block sizes, then the corresponding points between the blocks are always points of the same substances.

The block pair detector 343 sends, to the image averaging processor 344, position information indicating the positions of the target child block 1211 and the detected parent block 1214, which is similar to the target child block 1211, in the reconstructed image 1201.

Figure 17:
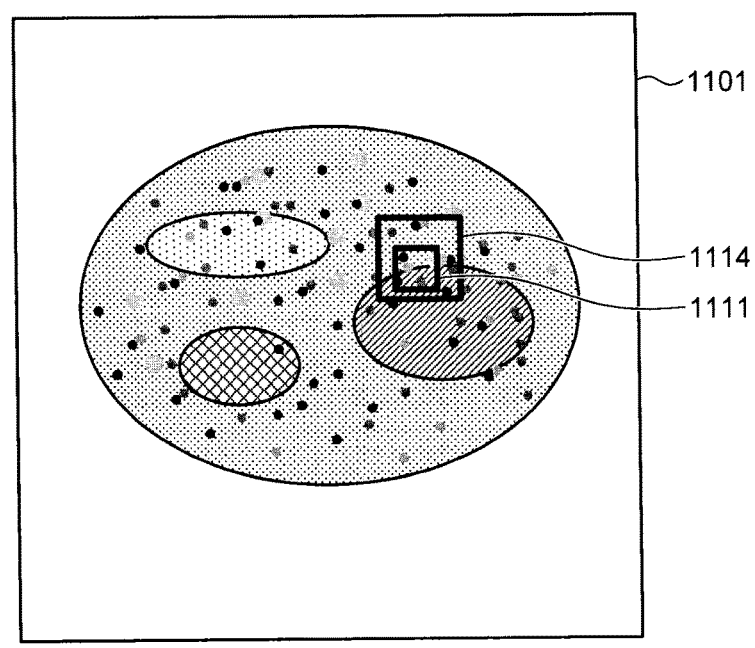
FIG. 17 is a diagram illustrating an example in which a block pair is placed in a reconstructed image corresponding to a specific energy.
Figure 18:
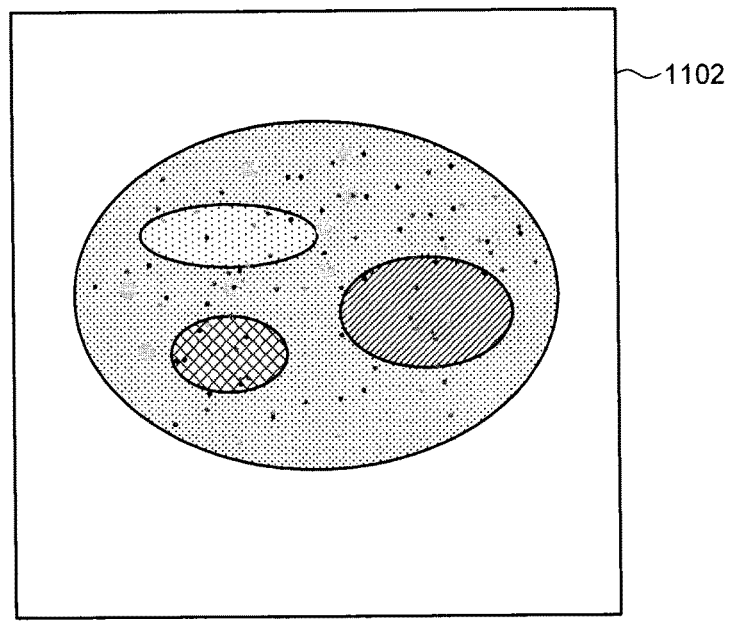
FIG. 18 is a diagram of a reconstructed image after weighted averaging of pixel values is performed with respect to a child block and a reduced block.
Figure 19:
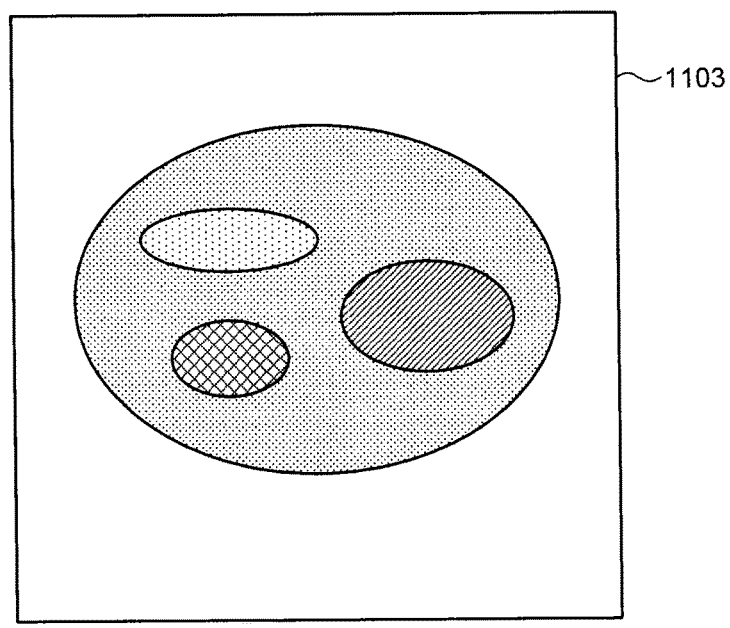
FIG. 19 is a diagram illustrating an example of a restored image obtained by performing weighted averaging in a repeated manner.

FIG. 17 is a diagram illustrating an example in which a block pair is placed in a reconstructed image corresponding to a specific energy. FIG. 18 is a diagram of a reconstructed image after weighted averaging of pixel values is performed with respect to a child block and a reduced block. FIG. 19 is a diagram illustrating an example of a restored image obtained by performing weighted averaging in a repeated manner. Thus, explained below with reference to FIGS. 17 to 19 is an averaging process performed by the image averaging processor 344 of the image processor 34 according to the first embodiment.

As described above, the reconstructed image 1101, which is generated as illustrated in FIG. 6 by the first reconstructor 341 based on the subject sinogram of a specific energy of the desired type (the energy of interest), has a greater variability in the pixel values as compared to the reconstructed image 1201 illustrated in FIG. 7. However, the reconstructed images 1101 and 1201 are images obtained from the same spectrum represented by the energy-by-energy photon count of the X-rays. Therefore, in the reconstructed image 1101 illustrated in FIG. 6, the position and the shape of each substance is identical to that in the reconstructed image 1201 illustrated in FIG. 7. Moreover, in the reconstructed image 1101 illustrated in FIG. 6, the average pixel value of each substance is ought to be almost identical to the linear attenuation coefficient in the specific energy of the desired type (the energy of interest). However, as described above, since the reconstructed image 1101 has a high degree of variability in the pixel values, there are times when the boundaries between the substances are ill-defined. In that regard, in the first embodiment, as a result of the detection of block pairs performed by the block pair detector 343 and the averaging process (described below) performed by the image averaging processor 344, a sharp restored image is obtained from the reconstructed image 1101.

In the reconstructed image 1101 received from the first reconstructor 341, the image averaging processor 344 identifies, as illustrated in FIG. 17, a block pair (of a child block 1111 (a third block) and a parent block 1114 (a fourth block)) at the position corresponding to the position indicated by the position information about block pairs that is received from the block pair detector 343. At this stage, the pixel values in the child block 1111 and the parent block 1114 are identical to the pixel values in the corresponding portion illustrated in FIG. 6.

Then, the image averaging processor 344 performs a reduction process in an identical manner as explained earlier with reference to FIGS. 10 to 12, and reduces the parent block 1114 to a reduced block having the same size as the child block 1111. Subsequently, using pixel values a1 to a4 of four pixels in the child block 1111 and using pixel values b1 to b4 of four pixels in the reduced block, the image averaging processor performs weighted averaging as given below in Equation (3).

$$\left.\begin{array}{l}c1 = \alpha \times a1 + (1-\alpha) \times b1 \\ c2 = \alpha \times a2 + (1-\alpha) \times b2 \\ c3 = \alpha \times a3 + (1-\alpha) \times b3 \\ c4 = \alpha \times a4 + (1-\alpha) \times b4\end{array}\right\} \quad (3)$$

In Equation (3), α represents the weight of pixel values and is a positive value such as 0.25, 0.5, or 0.75. Moreover, the weight α is decided by performing adjustment according to the variability in the pixel values. The image averaging processor 344 replaces the pixel values a1 to a4 of the four pixels in the child block 1111 of the reconstructed image 1101 with values c1 to c4 that are calculated by means of weighted averaging according to Equation (3), and sets the values c1 to c4 as the new pixel values. As far as weighted averaging and replacing the pixel values is concerned, the image averaging processor 344 performs those operations at each position indicated by the position information about child blocks that is received from the block pair detector 343 (i.e., performs those operations for each child block of the reconstructed image 1101). When the operation of weighted averaging and replacing the pixel values is performed once for each child block of the reconstructed image 1101 by the image averaging processor 344; a reconstructed image 1102 illustrated in FIG. 18 is obtained, for example.

As described above, in the reconstructed image 1101 (see FIG. 6) that is reconstructed at a specific energy, the position and the shape of each substance is identical to that in the reconstructed image 1201 (see FIG. 7). Therefore, in the reconstructed image 1101 too, the child block 1111 and the parent block 1114 are similar to each other. Thus, while performing weighted averaging according to Equation (3) with respect to the child block 1111, even if the reduced block obtained by reducing the parent block 1114 is used by the image averaging processor 344, the averaging of pixel values in each substance is maintained because the weighted averaging is performed for the pixels in the same substances. Thus, the variability in the pixel values of the reconstructed image 1101 goes on decreasing. Consequently, by repeatedly performing weighted averaging with respect to the child block 1111 using the reduced block obtained by reducing the parent block 1114, the image averaging processor 344 generates, as illustrated in FIG. 19, a restored image 1103 in which the pixel values are correct linear attenuation coefficients of the substances. As a result of repeated weighted averaging performed by the image averaging processor 344, the pixel values in the restored image 1103 are averaged on a substance-by-substance basis. Hence, the variability in the pixel values decreases, and the accuracy of reconstruction can be enhanced. Meanwhile, the repetitive weighted averaging performed by the image averaging processor 344 with respect to the child block 1111 using a reduced block can be ended after a predetermined number of repetitions. Alternatively, when the difference between the pixel values replaced in the previous instance with the values obtained by weighted averaging and the values obtained in the current instance by weighted averaging (i.e., the average value or the total value of the difference between all pixels of a reconstructed image) becomes equal to or smaller than a predetermined threshold value, the repetitive weighted averaging can be ended.

Meanwhile, since the image averaging processor 344 generates a reduced block by reducing the parent block 1114 of the reconstructed image 1101, the low-frequency components of variability in the pixel values causing noise make a gradual transition to high-frequency components. Then, the reduced block including variability in the pixel values of high-frequency components is subjected to weighted averaging with respect to the child block 1111. That results in a decrease in the variability. That is, not only the high-frequency components of variability in the pixel values causing noise can be reduced, but also the low-frequency components can be reduced.

Moreover, in the reconstructed image 1101, averaging of pixel values is not done across the boundaries among the substances. Instead, the pixel values are averaged on a substance-by-substance basis. Hence, in the restored image 1103, the contrast among the substances is restored and the boundaries among the substances become sharp.

Subsequently, the image averaging processor 344 outputs the restored image 1103 to the image storage 35. Thus, the restored image 1103 is stored in the image storage 35.

Figure 20:
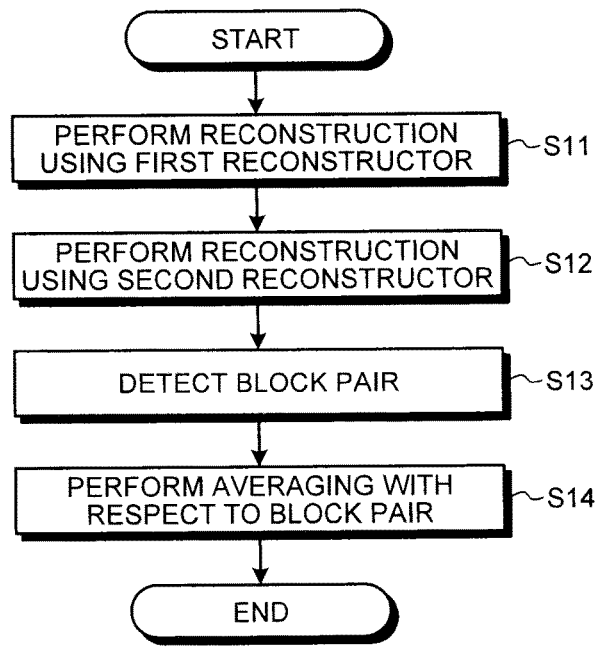
FIG. 20 is a flowchart for explaining the operations performed by the image processor according to the first embodiment.

FIG. 20 is a flowchart for explaining the operations performed by an image processor according to the first embodiment. Thus, explained below with reference to FIG. 20 are the overall operations during the image processing performed by the image processor 34 according to the first embodiment.

Step S11

The first reconstructor 341 receives data of the spectrum which is detected on a channel-by-channel basis by the detector 13, which is represented by the energy-by-energy photon count of the X-rays that have passed through the subject 40, and which is collected by the data collector 16. Then, from the received spectrum, the first reconstructor 341 generates a subject sinogram of a specific energy of the desired type (the energy of interest), and generates an attenuation fraction sinogram based on the subject sinogram. Subsequently, the first reconstructor 341 reconstructs the generated attenuation sinogram and generates the reconstructed image 1101 (see FIG. 6) having linear attenuation coefficients as pixel values; and sends the reconstructed image 1101 to the image averaging processor 344. Then, the system control proceeds to Step S12.

Step S12

The second reconstructor 342 receives input of data of the spectrum which is detected on a channel-by-channel basis by the detector 13, which is represented by the energy-by-energy photon count of the X-rays that have passed through the subject 40, and which is collected by the data collector 16. Then, the second reconstructor 342 generates, from the received spectrum, a subject sinogram of either a plurality of energies of the spectrum or all energies of the spectrum. The second reconstructor 342 reconstructs the subject sinogram and generates the reconstructed image 1201 (see FIG. 17), and sends the reconstructed image 1201 to the block pair detector 343. Then, the system control proceeds to Step S13.

Step S13

The block pair detector 343 divides the reconstructed image 1201 into the child blocks 1201a segmented in a reticular pattern as illustrated in FIG. 8. Then, for each target child block 1211 that is the target child block for processing from among the divided child blocks 1201a, the block pair detector 343 searches for the parent block 1212 that is larger than the concerned child block and that has a similar pattern of pixel values. Subsequently, the block pair detector 343 uses the pixel values of the pixels 1212a in the parent block 1212 and reduces the parent block 1212 to generate the reduced block 1213 having the same size as the target child block 1211. Then, using the pixel value of each pixel in the target child block 1211 and using the pixel value of each pixel in the reduced block 1213, the block pair detector 343 calculates, for example, the absolute value error according to Equation (1) given above or the squared error according to Equation (2) given above. Subsequently, the block pair detector 343 determines that, of a plurality of parent blocks 1212, the parent block 1212 corresponding to the reduced block 1213 having the smallest absolute value error is similar to the target child block 1211, and detects that particular parent block 1212 as the detected parent block 1214 (see FIG. 13). Then, the block pair detector 343 sends, to the image averaging processor 344, position information indicating the position of the block pair of the target child block 1211 and the detected parent block 1214, which is similar to the target child block 1211, in the reconstructed image 1201. The system control then proceeds to Step S14.

Step S14

In the reconstructed image 1101 received from the first reconstructor 341, the image averaging processor 344 identifies, as illustrated in FIG. 17, a block pair (the child block 1111 and the parent block 1114) at the position corresponding to the position indicated by the position information about block pairs that is received from the block pair detector 343. Then, the image averaging processor 344 performs a reduction process in an identical manner to the block pair detector 343, and reduces the parent block 1114 to a reduced block having the same size as the child block 1111. Subsequently, using the pixel values of the pixels in the child block 1111 and using the pixel values of the pixels in the reduced block, the image averaging processor performs weighted averaging according to Equation (3) given above. Then, the image averaging processor 344 replaces the pixel values of the pixels in the child block 1111 of the reconstructed image 1101 with values that are calculated by performing weighted averaging according to Equation (3) given above, and sets the substituted values as the new pixel values. As far as weighted averaging and replacing the pixel values is concerned, the image averaging processor 344 performs those operations at each position indicated by the position information about child blocks that is received from the block pair detector 343 (i.e., performs those operations for each child block of the reconstructed image 1101). With respect to the child block 1111, the image averaging processor 344 repeatedly performs weighted averaging using the reduced block obtained by reducing the parent block 1114, and generates the restored image 1103. Then, the image averaging processor 344 outputs the restored image 1103 to the image storage 35. Thus, the restored image 1103 is stored in the image storage 35.

As a result of such image processing performed by the image processor 34, the pixel values in the restored image 1103 are averaged on a substance-by-substance basis. Hence, the variability in the pixel values decreases, and the accuracy of reconstruction can be enhanced.

Moreover, since the image averaging processor 344 generates a reduced block by reducing the parent block 1114 in the reconstructed image 1101, the low-frequency components of variability in the pixel values causing noise make a gradual transition to high-frequency components. Then, the reduced block including variability in the pixel values of high-frequency components is subjected to weighted averaging with respect to the child block 1111. That results in a decrease in the variability. That is, not only the high-frequency components of variability in the pixel values causing noise can be reduced, but also the low-frequency components can be reduced.

Furthermore, in the reconstructed image 1101, averaging of pixel values is not done across the boundaries among the substances. Instead, the pixel values are averaged on a substance-by-substance basis. Hence, in the restored image 1103, the contrast among the substances is restored and the boundaries among the substances become sharp.

Meanwhile, although the second reconstructor 342 generates, from the received spectrum of X-rays, a subject sinogram of either a plurality of energies of the spectrum or all energies of the spectrum; that is not the only possible case. Alternatively, it is also possible to use the energy of characteristic X-rays (second energy) included in the X-rays. Herein, the characteristic X-rays represent the X-rays emitted during a process in which a radiation source called target installed in the X-ray tube 11 makes transition from a high electron level to a low electron level. Moreover, the energy of the characteristic X-rays is decided according to the substance of the target. For example, for tungsten, the energy of characteristic X-rays is known to be 59 [keV]. Furthermore, the characteristic X-rays have a particularly large photon count in, for example, the central part of the spectrum illustrated in FIG. 4. Thus, while passing through the subject 40, the photon count of the characteristic X-rays also decreases. However, since the photon count emitted from the X-ray tube 11 itself is large, usually the photon count of the characteristic X-rays reaching the detector 13 is also greater than other energies. Hence, as a result of using the photon count of the energy of the characteristic X-rays, it becomes possible to reconstruct an image having less variability in the pixel values. Meanwhile, the fact that, the greater the photon count of an energy band, the lower is the noise and higher is the signal-to-noise (S/N) ratio is not limited to the characteristic X-rays. Therefore, it is also effective if the second reconstructor 342 generates a reconstructed image using an energy band having a greater photon count than the energy band used by the first reconstructor 341 in generating a reconstructed image.

Meanwhile, the detector 13 detects the spectrum, which is represented by the energy-by-energy photon count, for each channel (detecting element) arranged in the circumferential direction of the rotating frame 12. However, as described above, the detector 13 has detecting elements arranged also in the body axis direction of the subject 40. Thus, a sinogram can be generated for each detecting element of a ring-like arrangement of detecting elements in the body axis direction, and image processing can be performed with respect to those sinograms. Alternatively, in the case of performing helical scanning in which the rotating frame 12 is continuously rotated while moving the top panel 22, instead of using only the data detected using the channels (the detecting elements) in the same circumferential direction, sinograms can be generated by performing interpolation using the data detected by the channels shifted in the body axis direction. Still alternatively, as in the case of a dual-energy X-ray CT scanner, the energy of the X-rays emitted from the X-ray tube 11 is divided into two types, and the types are switched every cycle for the emission purpose (for example, 40 [keV] in the first cycle, and 80 [keV] at the second cycle) so that a sinogram can be generated by combining the spectrums of different energies.

Meanwhile, the reconstructed image 1101, which is reconstructed by the first reconstructor 341, is assumed to have the pixel values in the form of linear attenuation coefficients. However, that is not the only possible case. Alternatively, as long as the values such as CT numbers (CT values) represent the amount of attenuation of the X-rays, it serves the purpose. Similarly, the pixel values of sinograms are also not limited to the photon count or the attenuation fraction. Alternatively, as long as the values represent the X-ray dose or the photon count or represent the rate of variability of the X-ray dose or the photon count, it serves the purpose.

Meanwhile, although the image processing for generating a restored image is explained with reference to the X-ray inspection device 1; any image processing device, such as an X-ray fluoroscope illustrated in FIG. 22, that is capable of obtaining images projecting or capturing a subject and having different photon counts can be used to perform the image processing.

First Modification Example

Figure 21:
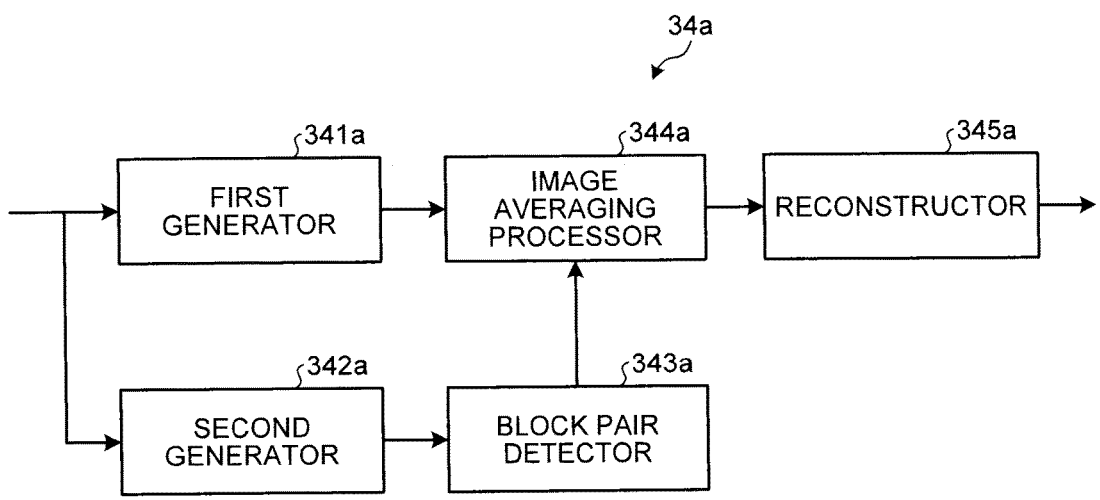
FIG. 21 is a block configuration diagram of an image processor according to a first modification example of the first embodiment.

FIG. 21 is a block configuration diagram of an image processor according to a first modification example of the first embodiment. Thus, explained below with reference to FIG. 21 is a configuration and the operations of an image processor 34a according to the first modification example. Herein, the explanation is given with the focus on the differences with the image processor 34 of the X-ray inspection device 1 according to the first embodiment. In the first embodiment, with respect to a reconstructed image that is reconstructed from a sinogram, image processing for reducing the variability is performed. In the first modification example, the explanation is given about an operation in which, after image processing for reducing the variability is performed with respect to a sinogram, the sinogram is reconstructed. Herein, an X-ray inspection device according to the first modification example is configured by replacing the image processor 34 illustrated in FIG. 1 with the image processor 34a.

As illustrated in FIG. 21, the image processor 34a includes a first generator 341a (a first generator), a second generator 342a (a second generator), a block pair detector 343a (a detector), an image averaging processor 344a (a corrector), and a reconstructor 345a (a reconstructor).

The first generator 341a is a processing unit that generates a subject sinogram (described later) from a spectrum represented by the energy-by-energy photon count of the X-rays, and generates an attenuation fraction sinogram (described later) (a first sinogram, a first image) based on the subject sinogram.

More particularly, the first generator 341a receives data of the spectrum which is detected on a channel-by-channel basis by the detector 13, which is represented by the energy-by-energy photon count of the X-rays that have passed through the subject 40, and which is collected by the data collector 16. Then, from the received spectrum, the first generator 341a generates a subject sinogram of a specific energy of the desired type (the energy of interest) (a first energy), and generates an attenuation fraction sinogram based on the subject sinogram. Subsequently, the first generator 341a sends the attenuation fraction sinogram to the image averaging processor 344a.

In this way, the first generator 341a generates a subject sinogram of a specific energy of the desired type from the spectrum represented by the energy-by-energy photon count of the X-rays. However, the photon count, which serves as the pixel values constituting the subject sinogram, is small. For that reason, the quantum fluctuation or the detector error has a significant impact. Hence, the attenuation fractions serving as the pixel values of the attenuation fraction sinogram include errors and exhibit high variability. Therefore, the attenuation fractions become values of low accuracy.

The second generator 342a is a processing unit that generates, from the spectrum represented by the energy-by-energy photon count of the X-rays, a subject sinogram (a second sinogram, a second image) in which the photon counts of a plurality of energies or the photon counts of all energies of the spectrum are added for each view and for each channel.

More particularly, the second generator 342a receives input of data of a spectrum which is detected on a channel-by-channel basis by the detector 13, which is represented by the energy-by-energy photon count of the X-rays that have passed through the subject 40, and which is collected by the data collector 16. Then, the second generator 342a generates, from the received spectrum, a subject sinogram of either a plurality of energies of the spectrum or all energies of the spectrum. Subsequently, the second generator 342a sends the subject sinogram to the block pair detector 343a.

In the subject sinogram generated by the second generator 342a, the pixel values represent values obtained by adding the photon counts of a plurality of energies of the spectrum or the photon counts of all energies of the spectrum. Thus, in the subject sinogram, the pixel values have less variability as compared to the attenuation fraction sinogram generated by the first generator 341a, but are different than the attenuation fraction at a specific energy.

The block pair detector 343a is a processing unit that divides the subject sinogram, which is received from the second generator 342a, into child blocks and detects parent blocks each of which is similar to one of the child blocks. The operation by which the block pair detector 343a detects parent blocks similar to a plurality of child blocks in a subject sinogram is identical to the operation by which the block pair detector 343 according to the first embodiment detects parent blocks similar to a plurality of child blocks in the reconstructed image 1201. Then, the block pair detector 343a sends, to the image averaging processor 344a, position information about block pairs of child blocks (first blocks) and the respective similar parent blocks (second blocks) in the subject sinogram.

The image averaging processor 344a is a processing unit that, in the attenuation fraction sinogram received from the first generator 341a, identifies a block pair at the position indicated by the position information about block pairs that is received from the block pair detector 343a; and performs an averaging process in which the pixel values are replaced with values obtained by performing weighted averaging of the pixel values of the child block (a third block) in the identified block pair and the pixel values of a reduced block obtained by reducing the parent block (a fourth block) in the identified block pair. As far as weighted averaging and replacing the pixel values is concerned, the image averaging processor 344a performs those operations at each position indicated by the position information about child blocks that is received from the block pair detector 343a (i.e., performs those operations for each child block of the attenuation fraction sinogram). With respect to the child blocks of the attenuation fraction sinogram, the image averaging processor 344a repeatedly performs weighted averaging using reduced blocks obtained by reducing the parent blocks, and generates an attenuation fraction sinogram in which the variability is reduced. Then, the image averaging processor 344a sends the attenuation fraction sinogram having a reduced variability to the reconstructor 345a.

The reconstructor 345a is a processing unit that reconstructs the attenuation fraction sinogram, which has a reduced variability and which is received from the image averaging processor 344a, and generates a reconstructed image (a restored image). Then, the reconstructor 345a outputs the reconstructed image to the image storage 35. Thus, the reconstructed image is stored in the image storage 35.

In this way, as a result of weighted averaging performed by the image averaging processor 344a, the variability is reduced in the attenuation fraction sinogram. Hence, the variability in the reconstructed image, which is reconstructed by the reconstructor 345a, also decreases, and the accuracy of reconstruction can be enhanced. Meanwhile, it is needless to say that the other effects achieved in the first embodiment are also achieved.

Herein, although the explanation is given for an example in which a process for reducing the variability is performed with respect to the attenuation fraction sinogram generated by the first generator 341a, that is not the only possible case. Alternatively, after a process for reducing the variability is performed with respect to a subject sinogram and an air sinogram, the first generator 341a can generate an attenuation fraction sinogram according to the subject sinogram and the air sinogram having a reduced variability.

Meanwhile, the first generator 341a, the second generator 342a, the block pair detector 343a, the image averaging processor 344a, and the reconstructor 345a in the image processor 34a can be implemented using software such as computer programs or can be implemented using hardware circuitry. Moreover, the first generator 341a, the second generator 342a, the block pair detector 343a, the image averaging processor 344a, and the reconstructor 345a in the image processor 34a illustrated in FIG. 21 represent only a conceptual illustration of the functions, and the configuration is not limited to that example.

Second Modification Example

Figure 22:
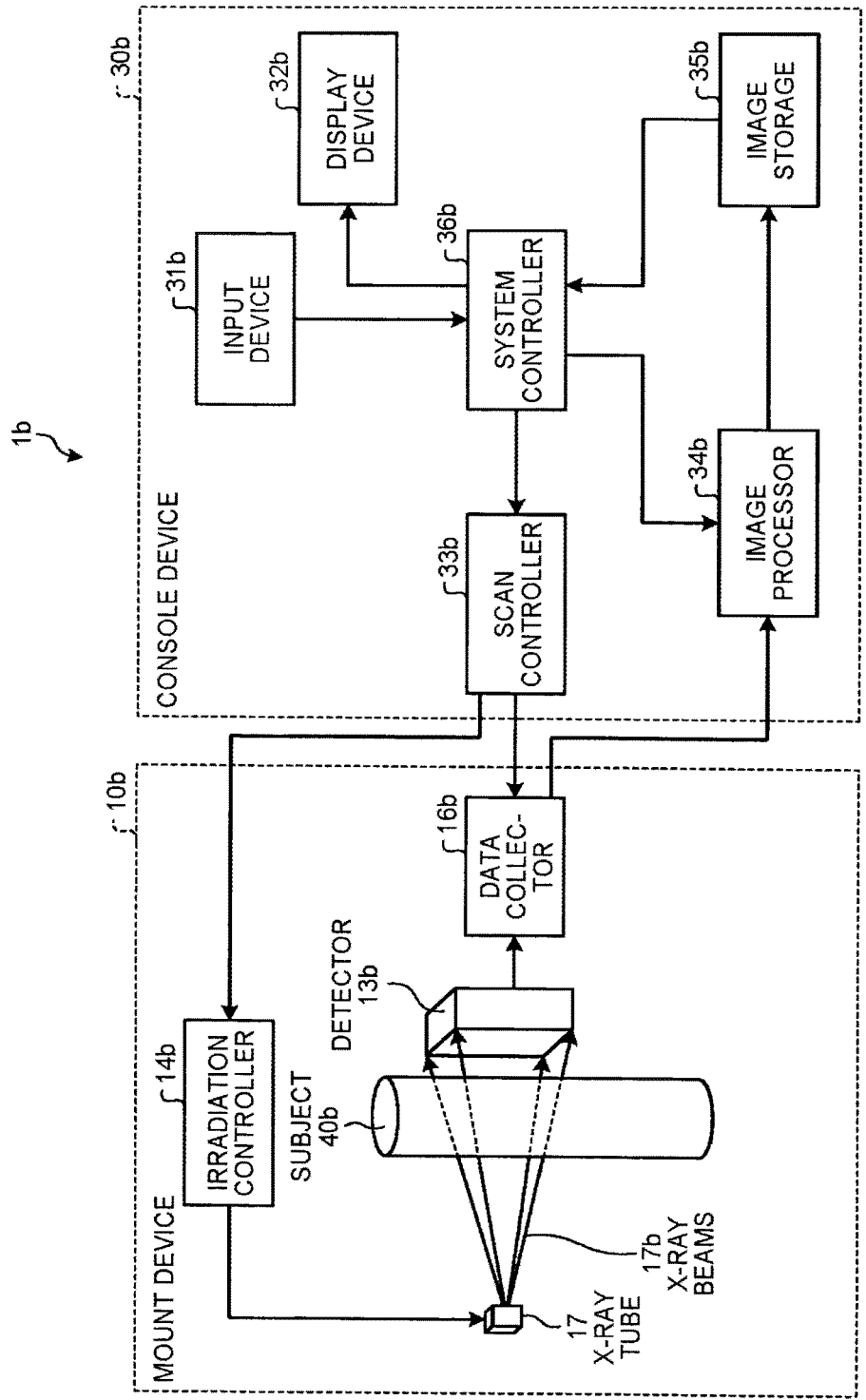
FIG. 22 is an overall configuration diagram of an X-ray fluoroscope according to a second modification example of the first embodiment.

FIG. 22 is an overall configuration diagram of an X-ray fluoroscope according to a second modification example of the first embodiment. Thus, explained below with reference to FIG. 22 is a configuration and the operations of an X-ray fluoroscope 1b according to the second modification example. Herein, the explanation is given with the focus on the differences with the X-ray inspection device 1 according to the first embodiment. In the first embodiment, image processing for reducing the variability is performed with respect to a reconstructed image that is reconstructed from a sinogram. In the second modification example, the explanation is given about a case in which image processing for reducing the variability is performed with respect to a perspective image.

The X-ray fluoroscope 1b, which is an example of a radiation detecting device, is a device in which X-rays, which are an example of radiation, are passed through a subject 40b and are detected as a spectrum represented by an energy-by-energy photon count; and a perspective image of the subject 40b is obtained. As illustrated in FIG. 22, the X-ray fluoroscope 1b includes a mount device 10b and a console device 30b.

The mount device 10b is a device that bombards the subject 40b with X-rays so that the X-rays pass through the subject 40b, and detects the spectrum mentioned above. The mount device 10b includes an X-ray tube 17 (an example of a radiation tube), a detector 13b, an irradiation controller 14b, and a data collector 16b.

The X-ray tube 17 is a vacuum tube for generating X-rays in response to a high voltage supplied from the irradiation controller 14b, and bombarding the subject 40b with X-ray beams 17b. The spectrum represented by the energy-by-energy photon count of the X-rays emitted from the X-ray tube 17 is determined according to the tube voltage of the X-ray tube 17, the tube current of the X-ray tube 17, and the type of target used in the radiation source (for example, tungsten is used). When the X-rays emitted from the X-ray tube 17 pass through the subject 40b, according to the condition of the substances constituting the subject 40b, the photon count of each energy decreases and the spectrum undergoes a change.

The detector 13b is a two-dimensional array type detector in which a plurality of detecting element arrays is arranged along the vertical direction and the horizontal direction. The detector 13b detects, at each detecting element, the energy-by-energy photon count of the X-rays that have been emitted from the X-ray tube 17 and that have passed through the subject 40b. That is, the detector 13b detects, at each of the detecting elements arranged in the vertical direction and the horizontal direction, a spectrum represented by the energy-by-energy photon count as illustrated in FIG. 4.

The irradiation controller 14 is a device that generates a high voltage and supplies it to the X-ray tube 17.

The data collector 16b is a device that collects data of the spectrum which is detected on a channel-by-channel basis by the detector 13 and which is represented by the energy-by-energy photon count. Moreover, the data collector 16b performs amplification and A/D conversion with respect to each set of collected data, and outputs the processed data to the console device 30b.

The console device 30b is a device that receives an operation performed by an operator with respect to the X-ray fluoroscope 1b, and generates a perspective image from the data collected by the mount device 10b. As illustrated in FIG. 22, the console device 30b includes an input device 31b, a display device 32b, a scan controller 33b, an image processor 34b, an image storage 35b, and a system controller 36b. The functions of the input device 31b, the display device 32b, the scan controller 33b, the image storage 35b, and the system controller 36b are identical to the functions of the input device 31, the display device 32, the scan controller 33, the image storage 35, and the system controller 36, respectively, illustrated in FIG. 1.

The image processor 34b is a processing unit that generates a perspective image based on the spectrum data collected by the data collector 16b. Regarding a block configuration and the operations of the image processor 34b, the details are given later.

Figure 23:
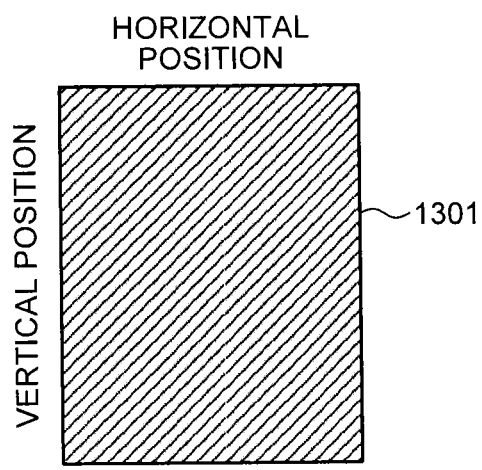
FIG. 23 is a diagram for explaining a perspective image.
Figure 24:
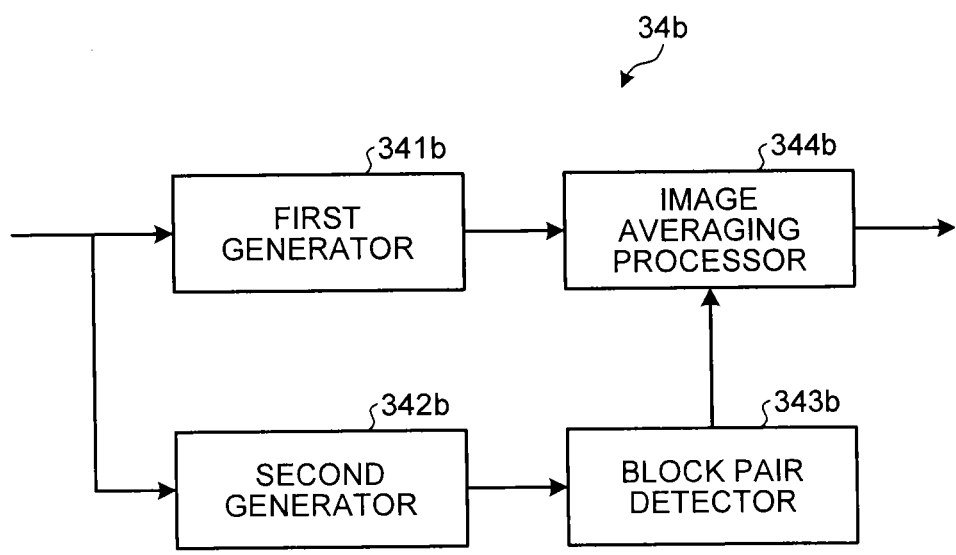
FIG. 24 is a block configuration diagram of an image processor according to the second modification example of the first embodiment.

FIG. 23 is a diagram for explaining a perspective image. FIG. 24 is a block configuration diagram of an image processor according to the second modification example of the first embodiment. Thus, explained below with reference to FIGS. 23 and 24 is a configuration and the operations of the image processor 34b.

As illustrated in FIG. 24, the image processor 34b includes a first generator 341b (a first generator), a second generator 342b (a second generator), a block pair detector 343b (a detector), and an image averaging processor 344b (a corrector).

The first generator 341b is a processing unit that generates a perspective image from the spectrum represented by the energy-by-energy photon count of the X-rays. Herein, in a perspective image, as in a perspective image 1301 illustrated in FIG. 23, the measured values at the detector elements, which are arranged in the vertical direction and the horizontal direction of the X-ray tube 17, serve as the pixel values. The pixel values of the perspective image 1301 are the photon counts detected as measured values by the detector 13b. Moreover, the detector 13b detects a spectrum, which is represented by the energy-by-energy photon count, for each detecting element arranged in the vertical direction and the horizontal direction. Therefore, in the X-ray fluoroscope 1b, when X-ray scanning is performed for one revolution of the X-ray tube 17, it is possible to obtain a perspective image for each energy in an identical manner to the case illustrated FIG. 5.

The first generator 341b receives data of the spectrum (identical to FIG. 4) which is detected at each detecting element by the detector 13, which is represented by the energy-by-energy photon count from the X-rays that have passed through the subject 40b, and which is collected by the data collector 16b. Then, from the received spectrum, the first generator 341b generates a perspective image (a first perspective image, a first image) of a specific energy of the desired type (the energy of interest) (a first energy); and sends the perspective image to the image averaging processor 344b. Meanwhile, the pixel values of a perspective image differ according to the type and the concentration of the substance through which the X-rays are passed. Hence, if the distribution of pixel values is made visible in a perspective image, then it enables recognition of the internal structure of the subject 40b. Moreover, the pixel values of a perspective image differ also according to the energies of the photons of X-rays. Hence, if a particular substance is to be observed, then the spectrum of an energy for which the difference in the pixel values with other substances is large can be used to enhance the contrast between substances. As a result, it becomes possible to obtain a perspective image having a high degree of visibility.

In this way, the first generator 341b generates, from the spectrum represented by the energy-by-energy photon count of the X-rays, a perspective image of a specific energy of the desired type. However, the photon count, which serves as the pixel values constituting the perspective image, is small. For that reason, the quantum fluctuation or the detector error has a significant impact. Hence, the pixel values of the generated perspective image include errors and exhibit high variability. Therefore, the pixel values become values of low accuracy.

The second generator 342b is a processing unit that, from the spectrum represented by the energy-by-energy photon count of the X-rays, generates a perspective image (a second perspective image, a second image) in which the photon counts of a plurality of energies of the spectrum or the photon counts of all energies of the spectrum (a second energy) are added at each detecting element in the vertical direction and the horizontal direction. Firstly, the second generator 342b receives data of the spectrum (identical to FIG. 4) which is detected at each detecting element by the detector 13b, which is represented by the energy-by-energy photon count from the X-rays that have passed through the subject 40b, and which is collected by the data collector 16b. Then, the second generator 342b generates, from the received spectrum, a perspective image of either a plurality of energies of the spectrum or all energies of the spectrum. Subsequently, the second generator 342b sends the perspective image to the block pair detector 343b. In the perspective image generated by the second generator 342b, the pixel values represent values obtained by adding the photon counts of a plurality of energies of the spectrum or the photon counts of all energies of the spectrum. Thus, in the perspective image, the pixel values have less variability as compared to the perspective image generated by the first generator 341b, but are different than the photon count at a specific energy.

The block pair detector 343b is a processing unit that divides the perspective image, which is received from the second generator 342b, into child blocks (first blocks) and detects parent blocks (second blocks) each of which is similar to one of the child blocks. Then, the block pair detector 343b sends position information about block pairs of child blocks and the respective similar parent blocks to the image averaging processor 344b. The image processing performed by the block pair detector 343b with respect to the perspective image received from the second generator 342b is identical to the image processing performed by the block pair detector 343 with respect to the reconstructed image 1201 (see FIG. 7).

The image averaging processor 344b is a processing unit that, in the perspective image received from the first generator 341b, identifies a block pair at the position indicated by the position information about block pairs that is received from the block pair detector 343b; and performs an averaging process in which the pixel values are replaced with values obtained by performing weighted averaging of the pixel values of the child block (a third block) in the identified block pair and the pixel values of a reduced block obtained by reducing the parent block (a fourth block) in the identified block pair. With respect to a child block, the image averaging processor 344b repeatedly performs weighted averaging using a reduced block obtained by reducing the parent block, and generates a restored image in which the pixel values correspond to each substance. As a result of repeated weighted averaging performed by the image averaging processor 344b, the pixel values in the restored image are averaged on a substance-by-substance basis. Hence, the variability in the pixel values decreases, and the accuracy of the pixel values of the perspective image can be enhanced. Then, the image averaging processor 344b outputs the restored image to the image storage 35 (see FIG. 1). Thus, the restored image is stored in the image storage 35. The averaging process performed by the image averaging processor 344b with respect to the perspective image is identical to the averaging process performed by the image averaging processor 344 with respect to the reconstructed image 1101 as described above.

In this way, as a result of the image processing performed by the image averaging processor 344b, the pixel values in the restored image are averaged on a substance-by-substance basis. Hence, the variability in the pixel values decreases, and the accuracy of the pixel values of the perspective image can be enhanced.

Meanwhile, since the image averaging processor 344b generates a reduced block by reducing a parent block in the perspective image received from the first generator 341b, the low-frequency components of variability in the pixel values causing noise make a gradual transition to high-frequency components. Then, the reduced block including variability in the pixel values of high-frequency components is subjected to weighted averaging with respect to the child block. That results in a decrease in the variability. That is, not only the high-frequency components of variability in the pixel values causing noise can be reduced, but also the low-frequency components can be reduced.

Moreover, in the perspective image received from the first generator 341b, averaging of pixel values is not done across the boundaries among the substances. Instead, the pixel values are averaged on a substance-by-substance basis. Hence, in the restored image, the contrast among the substances is restored and the boundaries among the substances become sharp.

Meanwhile, the first generator 341b, the second generator 342b, the block pair detector 343b, and the image averaging processor 344b in the image processor 34b can be implemented using software such as computer programs or can be implemented using hardware circuitry. Moreover, the first generator 341b, the second generator 342b, the block pair detector 343b, and the image averaging processor 344b in the image processor 34b illustrated in FIG. 24 represent only a conceptual illustration of the functions, and the configuration is not limited to that example.

Second Embodiment

Regarding an X-ray inspection device according to a second embodiment, the explanation is given with the focus on the differences with the X-ray inspection device 1 according to the first embodiment. Although the X-ray inspection device according to the second embodiment has an identical configuration to the X-ray inspection device 1 according to the first embodiment, the image processor 34 is replaced with an image processor 34c illustrated in FIG. 25 and described later. In the second embodiment, the explanation is given for a case in which, during the image processing performed by the image processor 34c, an averaging process with respect to an image and a reconstruction process according to the successive approximation are performed in a simultaneous manner.

Figure 25:
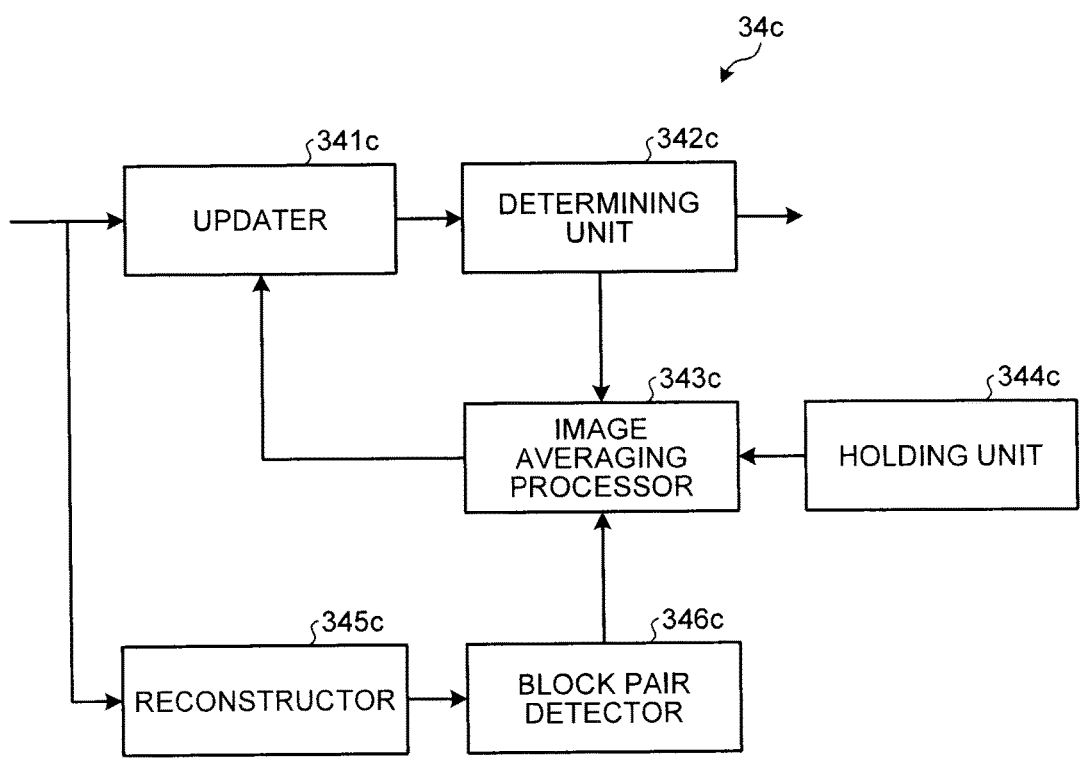
FIG. 25 is a block configuration diagram of an image processor according to a second embodiment.
Figure 26:
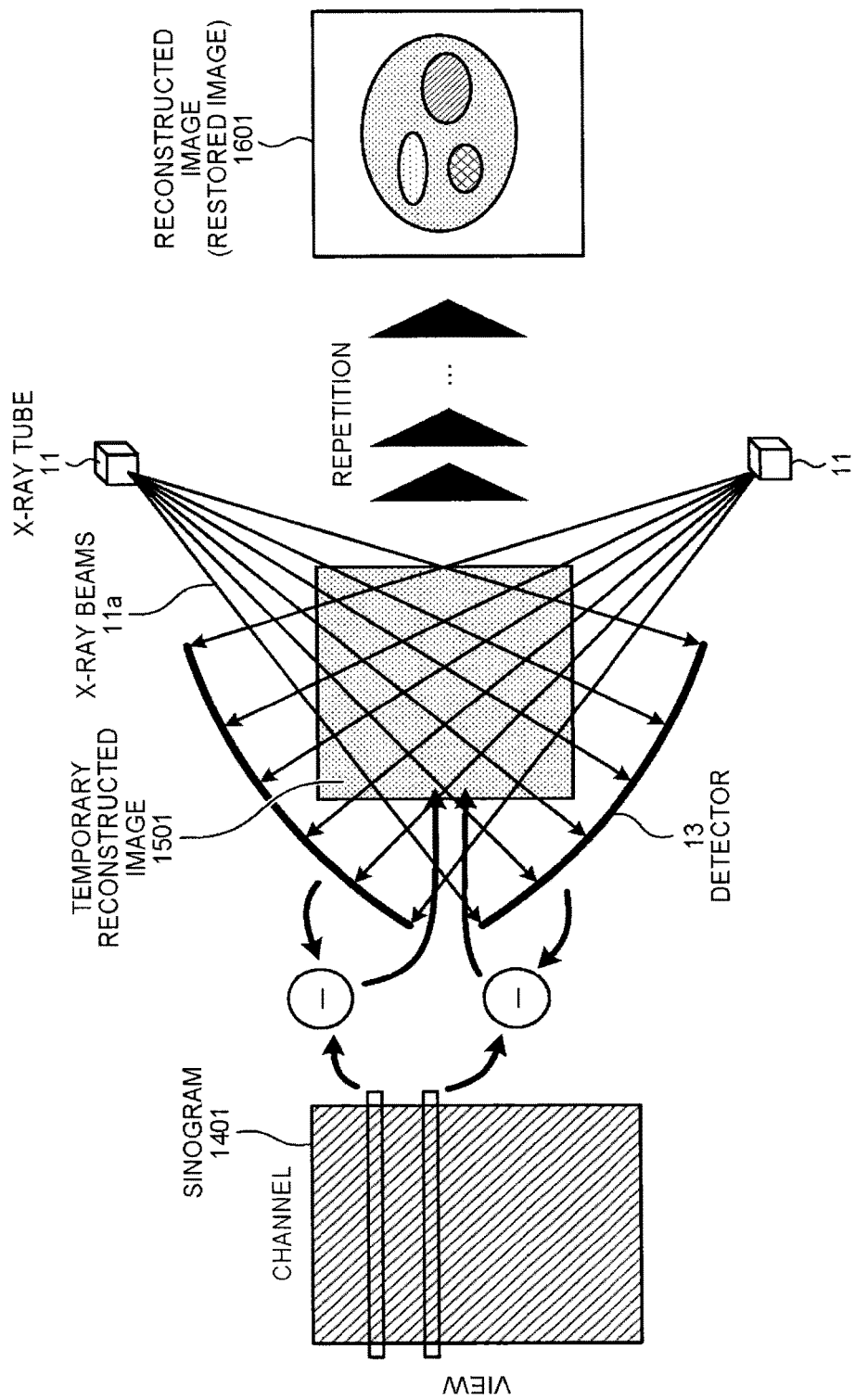
FIG. 26 is a diagram for explaining simultaneous execution of a successive-approximation-based operation and an averaging process.

FIG. 25 is a block configuration diagram of the image processor according to the second embodiment. FIG. 26 is a diagram for explaining simultaneous execution of a successive-approximation-based process and an averaging process. Thus, explained below with reference to FIGS. 25 and 26 is a configuration and the operations of the image processor 34c according to the second embodiment.

The image processor 34c is a processing unit that, based on the spectrum data collected by the data collector 16 (see FIG. 1), simultaneously performs an averaging process with respect to an image and a reconstruction process according to the successive approximation. Firstly, explained with reference to FIG. 26 is the simultaneous execution of an averaging process and a reconstruction process performed during the image processing by the image processor 34c.

According to the second embodiment, in the reconstruction process according to the successive approximation, firstly, a temporary reconstructed image 1501 (a first temporary reconstructed image) is provided in which temporary linear attenuation coefficients are arranged as the pixel values. Examples of temporary linear attenuation coefficients include setting a uniform value at all pixels or setting, in a circle formed by approximation of a separately-estimated profile of a subject, values greater than zero on the inside of the circle and setting zero on the outside of the circle.

Then, at the same positional relationship as the positional relationship in the case when the photon count in each view of a subject sinogram 1401 is detected due to the X-ray beams 11a emitted from the X-ray tube 11 and reaching the detector 13, when linear attenuation coefficients serve as the pixel values of the pixels of the temporary reconstructed image 1501, the image processor 34c calculates the photon count that is supposed to be detected by the detector 13. If the calculated photon count is different than the actual photon count detected by the detector 13, then the image processor 34c updates the pixel values of the temporary reconstructed image 1501. However, if there is no difference in the photon counts, the image processor 34c does not update the pixel values. Regarding the determination of whether or not the photon counts are different, for example, a predetermined threshold value can be set and if the difference in the photon counts is equal to or smaller than the threshold value, then it can be determined that there is no difference. In this way, corresponding to each view of the subject sinogram 1401, the image processor 34c performs the reconstruction process for updating the pixel values of the temporary reconstructed image 1501, and obtains a reconstructed image 1601 (a restored image) in which the linear attenuation coefficients are restored.

In such a reconstruction process according to the successive approximation, although the example of using the subject sinogram 1401 is given, it is also possible to use an attenuation fraction sinogram or to use a combination of an air sinogram and the subject sinogram 1401. Regarding the method of updating the pixel values of the temporary reconstructed image 1501, various methods are available. As an example, the explanation is given about a method of updating the pixel values according to a convex method using Equation (4) given below. The image processor 34c updates the pixel values of the temporary reconstructed image 1501 using linear attenuation coefficients $f_j$ obtained according to Equation (4) given below.

$$f_j^{k+1} = \frac{1}{1 + \beta \cdot V(f_j^k)} \left[ f_j^k + \frac{f_j^k \sum_i C_{ij} \left[ B_i e^{-\sum_{m \in l_i} C_{im} f_m^k} - T_i \right]}{\sum_i C_{ij} [\sum_{m \in l_i} C_{im} f_m^k] B_i e^{-\sum_{m \in l_i} C_{im} f_m^k}} \right] \quad (4)$$

In Equation (4), $f_j$ represents a linear attenuation coefficient, which is the pixel value (the updated value) of a pixel j of the temporary reconstructed image 1501; and the subscripted character (k or k+1) represents the updating count up to that time. Moreover, $I_i$ represents a pixel through which passes the X-ray beam 11a reaching the detecting element of a channel i. Furthermore, $C_{ij}$ represents a contribution ratio of the pixel j to the X-ray beams 11a reaching the channel i. For example, $C_{ij}$ represents the length or the area of the X-ray beams 11a cutting across the pixels. Moreover, $B_i$ represents the detected photon count of the X-ray beam 11a emitted from the X-ray tube 11 toward the channel i, that is, represents the pixel values of an air sinogram. Furthermore, $T_i$ represents the detected photon count of the X-ray beams 11a, which are emitted from the X-ray tube 11 toward the channel i and which have passed through the subject 40, at a specific energy of the desired type (the energy of interest). That is, $T_i$ represents the pixel value of the subject sinogram at the specific energy. Moreover, V represents a function for processing the temporary reconstructed image 1501 at the updating count up to that time, and $\beta$ represents an adjustment parameter with respect to the function V.

Herein, in the conventional convex method, the function V is obtained according to Equation (5) given below using a median filter.

$$V(f_j^k) = \frac{f_j^k - M_j}{M_j} \quad (5)$$

In Equation (5), $M_j$ represents the pixel value of an image obtained by performing filter processing using a median filter with respect to the temporary reconstructed image 1501 that has been updated for k number of times. A median filter is suitable in removing the spike-like noise or, what is called, the pepper and salt noise. However, a negative effect of blurring also occurs in the image after filter processing. In that regard, in the second embodiment, instead of using an image with respect to which filter processing is performed using a median filter, an image is used which is obtained by performing the abovementioned averaging process with respect to the temporary reconstructed image 1501 updated for k number of times, and pixel values $S_j$ of that image are used to calculate the function V according to Equation (6) given below.

$$V(f_j^k) = \frac{f_j^k - S_j}{S_j} \quad (6)$$

The image processor 34c updates the pixel values of the temporary reconstructed image 1501 using the linear attenuation coefficients $f_j$ calculated using Equations (4) and (6). In this way, using an image obtained by performing the averaging process in an identical manner to the first embodiment, a reconstruction process is performed in which updating is repeated using the linear attenuation coefficients $f_j$ according to Equations (4) and (6). As a result, in the reconstructed image 1601 (the restored image), the pixel values are averaged on a substance-by-substance basis. Hence, in the reconstructed image 1601, the variability in the pixel values decreases, and the accuracy of reconstruction can be enhanced.

Meanwhile, the equation for updating the pixel values of the temporary reconstructed image 1501 is not limited to Equation (4) given above. Alternatively, the pixel values can be updated based on other methods of the successive approximation.

Explained below in detail and with reference to FIG. 25 is a configuration and the operations of the image processor 34c. As illustrated in FIG. 25, the image processor 34c includes an updater 341c (a first generator), a determining unit 342c, an image averaging processor 343c (a corrector), a holding unit 344c, a reconstructor 345c (a second generator), and a block pair detector 346c (a detector).

The updater 341c is a processing unit that updates the pixel values of the temporary reconstructed image 1501 using the data of the spectrum represented by the energy-by-energy photon count of the X-rays as detected by the detector 13 and using the pixel values $S_j$ of the image received from the image averaging processor 343c after being subjected to the averaging process. Firstly, the updater 341c receives data of the spectrum (see FIG. 4) which is detected on a channel-by-channel basis by the detector 13, which is represented by the energy-by-energy photon count of the X-rays that have passed through the subject 40, and which is collected by the data collector 16. Then, from the received spectrum, the updater 341c generates a subject sinogram of a specific energy of the desired type (the energy of interest) (a first energy). Moreover, the updater 341c generates and stores an air sinogram in advance. Furthermore, the updater 341c receives, from the image averaging processor 343c, an image obtained by performing the averaging process with respect to the temporary reconstructed image 1501.

Then, using the pixel values of the subject sinogram and the pixel values of the air sinogram and using the pixel values $S_j$ of the image subjected to the averaging process by the image averaging processor 343c, the updater 341c calculates the linear attenuation coefficients according to Equations (4) and (6) given above. Subsequently, the updater 341c updates the pixel values of the temporary reconstructed image 1501 with the linear attenuation coefficients $f_j$ and generates a new temporary reconstructed image 1501. Then, the updater 341c sends the new temporary reconstructed image 1501 (a second temporary reconstructed image, a first image) to the determining unit 342c.

The determining unit 342c is a processing unit that determines whether or not the updater 341c has updated the temporary reconstructed image 1501 for a predetermined number of times. If the updater 341c has updated the temporary reconstructed image 1501 for a predetermined number of times, then the determining unit 342c outputs, to the image storage 35, the temporary reconstructed image 1501 at that point of time as the reconstructed image 1601 (the restored image). Thus, the reconstructed image 1601 output from the determining unit 342c is stored in the image storage 35. However, if the updater 341c has not yet updated the temporary reconstructed image 1501 for a predetermined number of times, then the determining unit 342c sends the temporary reconstructed image 1501, which is received from the updater 341c, to the image averaging processor 343c.

Herein, the determining unit 342c determines whether or not the updating operation is performed for a predetermined number of times. However, that is not the only possible case. Alternatively, at the point of time when the difference between the pixel values of the temporary reconstructed image 1501 updated in the previous instance by the updater 341c and the pixel values of the temporary reconstructed image 1501 that is newly received from the updater 341c (i.e., the average value or the total value of all pixel values of the temporary reconstructed image 1501) is equal to or smaller than a predetermined threshold value, the determining unit 342c can treat the temporary reconstructed image 1501 at that point of time as the reconstructed image 1601 (the restored image).

The image averaging processor 343c is a processing unit that, in the temporary reconstructed image 1501, identifies a block pair at the position corresponding to the position indicated by the position information about block pairs that is received from the block pair detector 346c; and performs an averaging process in which the pixel values are replaced with values obtained by performing weighted averaging of the pixel values of the child block (a third block) in the identified block pair and the pixel values of a reduced block obtained by reducing the parent block (a fourth block) in the identified block pair. Firstly, the image averaging processor 343c receives the temporary reconstructed image 1501 held by the holding unit 344c; arranges, in the temporary reconstructed image 1501, the block pair at the position indicated by the position information of block pairs that is received from the block pair detector 346c; and performs weighted averaging with respect to the block pair. Then, the image averaging processor 343c sends, to the updater 341c, an image that has been subjected to weighted averaging (the averaging process). Subsequently, in the temporary reconstructed image 1501 received from the determining unit 342c, the image averaging processor 343c arranges the block pair at the position indicated by the position information of block pairs that is received from the block pair detector 346c; and performs weighted averaging with respect to the block pair. Then, the image averaging processor 343c sends, to the updater 341c, an image that has been subjected to weighted averaging (the averaging process). Herein, the averaging process performed by the image averaging processor 343c with respect to the temporary reconstructed image 1501 is identical to the averaging process performed by the image averaging processor 344 with respect to the reconstructed image 1101 as described above.

The holding unit 344c holds the temporary reconstructed image 1501 in which temporary linear attenuation coefficients are arranged as the pixel values as illustrated in FIG. 26. The holding unit 344c sends the temporary reconstructed image 1501 when the image averaging processor 343c performs weighted averaging for the first time.

The reconstructor 345c is a processing unit that, from the spectrum represented by the energy-by-energy photon count of the X-rays, generates a subject sinogram in which the photon counts of a plurality of energies or the photon counts of all energies of the spectrum are added for each view and for each channel; and generates the reconstructed image 1201 (see FIG. 7) by reconstructing the subject sinogram. Firstly, the reconstructor 345c receives input of data of the spectrum (see FIG. 4) which is detected on a channel-by-channel basis by the detector 13, which is represented by the energy-by-energy photon count of the X-rays that have passed through the subject 40, and which is collected by the data collector 16. Then, the reconstructor 345c generates, from the received spectrum, a subject sinogram of either a plurality of energies of the spectrum or all energies of the spectrum. The reconstructor 345c implements the back projection method or the successive approximation to reconstruct the subject sinogram, and generates the reconstructed image 1201 (see FIG. 7) (a second image). Then, the reconstructor 345c sends the reconstructed image 1201 to the block pair detector 346c.

The block pair detector 346c is a processing unit that divides the reconstructed image 1201, which is received from the reconstructor 345c, into child blocks (first blocks) and detects parent blocks (second blocks) each of which has a similar pattern of pixel values to one of the child blocks. Then, the block pair detector 346c sends position information about block pairs of child blocks and the respective similar parent blocks to the image averaging processor 343c. Herein, the image processing performed by the block pair detector 346c with respect to the reconstructed image 1201 received from the reconstructor 345c is identical to the image processing performed by the block pair detector 343 with respect to the reconstructed image 1201 as described above.

Meanwhile, the updater 341c, the determining unit 342c, the image averaging processor 343c, the holding unit 344c, the reconstructor 345c, and the block pair detector 346c included in the image processor 34c can be implemented using software such as computer programs or can be implemented using hardware circuitry. Moreover, the updater 341c, the determining unit 342c, the image averaging processor 343c, the holding unit 344c, the reconstructor 345c, and the block pair detector 346c included in the image processor 34c illustrated in FIG. 25 represent only a conceptual illustration of the functions, and the configuration is not limited to that example.

Figure 27:
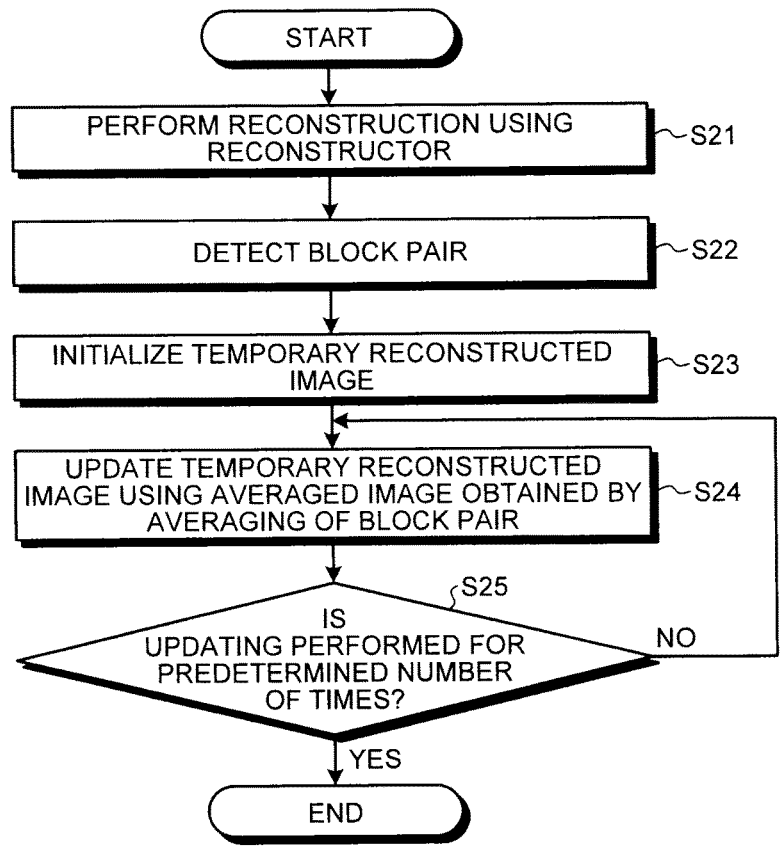
FIG. 27 is a flowchart for explaining the operations performed by an image processor according to the second embodiment.

FIG. 27 is a flowchart for explaining the operations performed by an image processor according to the second embodiment. Thus, explained below with reference to FIG. 27 are the overall operations during the image processing performed by the image processor 34c according to the second embodiment.

Step S21

The reconstructor 345c receives data of the spectrum which is detected on a channel-by-channel basis by the detector 13, which is represented by the energy-by-energy photon count of the X-rays that have passed through the subject 40, and which is collected by the data collector 16. Then, from the received spectrum, the reconstructor 345c generates a subject sinogram of either a plurality of energies of the spectrum or all energies of the spectrum. Subsequently, the reconstructor 345c reconstructs the subject sinogram and generates the reconstructed image 1201 (see FIG. 7), and sends the reconstructed image 1201 to the block pair detector 346c. Then, the system control proceeds to Step S22.

Step S22

The block pair detector 346c divides the reconstructed image 1201, which is received from the reconstructor 345c, into child blocks and detects parent blocks each of which has a similar pattern of pixel values to one of the child blocks. Then, the block pair detector 346c sends position information about block pairs of child blocks and the respective similar parent blocks to the image averaging processor 343c. The system control then proceeds to Step S23.

Step S23

The image averaging processor 343c receives the temporary reconstructed image 1501, in which temporary linear attenuation coefficients are arranged as the pixel values, from the holding unit 344c and initializes the temporary reconstructed image 1501. Then, the system control proceeds to Step S24.

Step S24

The image averaging processor 343c is a processing unit that, in the temporary reconstructed image 1501, arranges a block pair at the position corresponding to the position indicated by the position information about block pairs that is received from the block pair detector 346c; and performs an averaging process in which the pixel values are replaced with values obtained by weighted averaging of the pixel values of the child block in the block pair and the pixel values of a reduced block obtained by reducing the parent block in the block pair. In the temporary reconstructed image 1501 received from the holding unit 344c or the determining unit 342c, the image averaging processor 343c arranges a block pair at the position corresponding to the position indicated by the position information about block pairs that is received from the block pair detector 346c; and performs weighted averaging with respect to the block pair. Then, the image averaging processor 343c sends, to the updater 341c, an image that has been subjected to weighted averaging (the averaging process).

The updater 341c receives data of the spectrum which is detected on a channel-by-channel basis by the detector 13, which is represented by the energy-by-energy photon count of the X-rays that have passed through the subject 40, and which is collected by the data collector 16. Then, from the received spectrum, the updater 341c generates a subject sinogram of a specific energy of the desired type (a first energy). Moreover, the updater 341c generates and stores an air sinogram in advance. Furthermore, the updater 341c receives, from the image averaging processor 343c, an image obtained by performing the averaging process with respect to the temporary reconstructed image 1501. Then, using the pixel values of the subject sinogram and the pixel values of the air sinogram and using the pixel values $S_j$ of the image subjected to the averaging process by the image averaging processor 343c, the updater 341c calculates the linear attenuation coefficients $f_j$ according to Equations (4) and (6) given above. Subsequently, the updater 341c updates the pixel values of the temporary reconstructed image 1501 with the linear attenuation coefficients $f_j$ and generates a new temporary reconstructed image 1501. Then, the updater 341c sends the new temporary reconstructed image 1501 to the determining unit 342c. The system control then proceeds to Step S25.

Step S25

The determining unit 342c determines whether or not the updater 341c has updated the temporary reconstructed image 1501 for a predetermined number of times. If the updater 341c has not yet updated the temporary reconstructed image 1501 for a predetermined number of times (No at Step S25), then the determining unit 342c sends the temporary reconstructed image 1501, which is received from the updater 341c, to the image averaging processor 343c. The system control then returns to Step S24. On the other hand, if the updater 341c has updated the temporary reconstructed image 1501 for a predetermined number of times (Yes at Step S25), then the determining unit 342c outputs, to the image storage 35, the temporary reconstructed image 1501 at that point of time as the reconstructed image 1601 (the restored image). Thus, the reconstructed image 1601 output from the determining unit 342c is stored in the image storage 35. That marks the end of the image processing performed by the image processor 34c.

As a result of such image processing performed by the image processor 34, the pixel values in the reconstructed image 1601 are averaged on a substance-by-substance basis. Hence, the variability in the pixel values decreases, and the accuracy of reconstruction can be enhanced.

Moreover, since the image averaging processor 343c generates a reduced block by reducing the parent block in the temporary reconstructed image 1501, the low-frequency components of variability in the pixel values causing noise make a gradual transition to high-frequency components. Then, the reduced block including variability in the pixel values of high-frequency components is subjected to weighted averaging with respect to the child block. That results in a decrease in the variability. That is, not only the high-frequency components of variability in the pixel values causing noise can be reduced, but also the low-frequency components can be reduced.

Furthermore, in the temporary reconstructed image 1501, averaging of pixel values is not done across the boundaries among the substances. Instead, the pixel values are averaged on a substance-by-substance basis. Hence, in the reconstructed image 1601, the contrast among the substances is restored and the boundaries among the substances become sharp.

Third Embodiment

Regarding an X-ray inspection device according to a third embodiment, the explanation is given with the focus on the differences with the X-ray inspection device 1 according to the first embodiment. Herein, the X-ray inspection device according to the third embodiment has an identical configuration to the X-ray inspection device 1 according to the first embodiment. In the first embodiment, during the image processing performed by the image processor 34, the explanation is given about an operation of detecting block pairs each including a child block and a parent block that is greater in size than the child block. In contrast, in the third embodiment, during the image processing performed by the image processor 34, the explanation is given about an operation of detecting block pairs each including a child block and a parent block that is equal in size to the child block.

In an identical manner to the image processor 34 illustrated in FIG. 2 according to the first embodiment, the image processor 34 according to the third embodiment includes the first reconstructor 341 (a first generator), the second reconstructor 342 (a second generator), the block pair detector 343 (a detector), and the image averaging processor 344 (a corrector). The operations performed by the first reconstructor 341 and the second reconstructor 342 are identical to the first embodiment. However, an image reconstructed by the second reconstructor 342 is assumed to be a reconstructed image 1701 (a second image) illustrated in FIG. 28 (described below).

Figure 28:
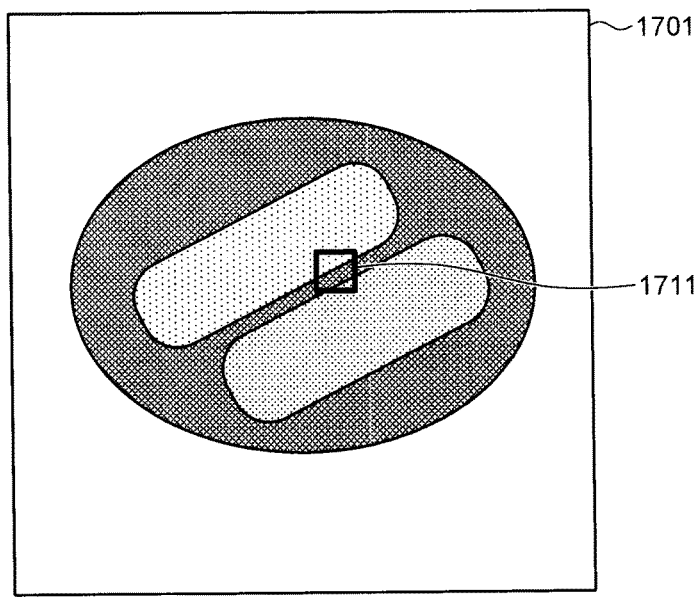
FIG. 28 is a diagram illustrating an exemplary child block in a reconstructed image.
Figure 29:
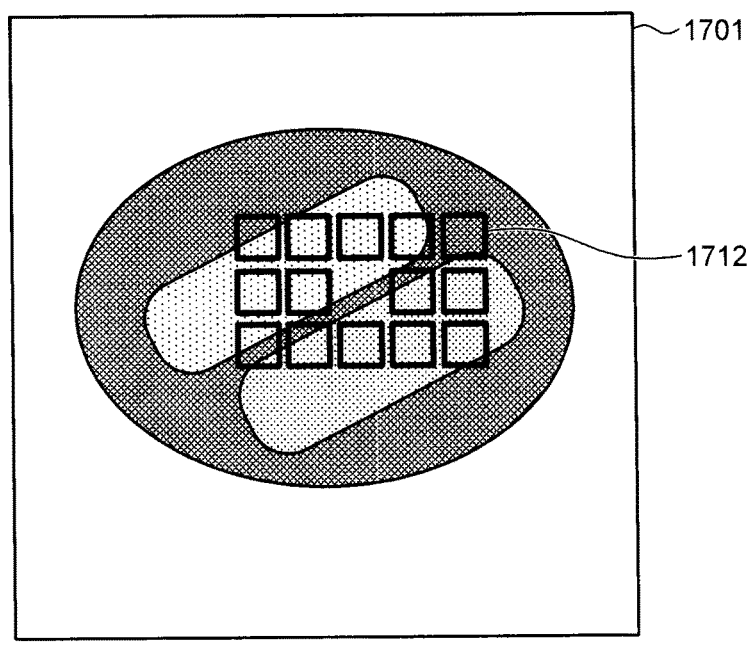
FIG. 29 is a diagram illustrating exemplary parent blocks set around a target child block.
Figure 30:
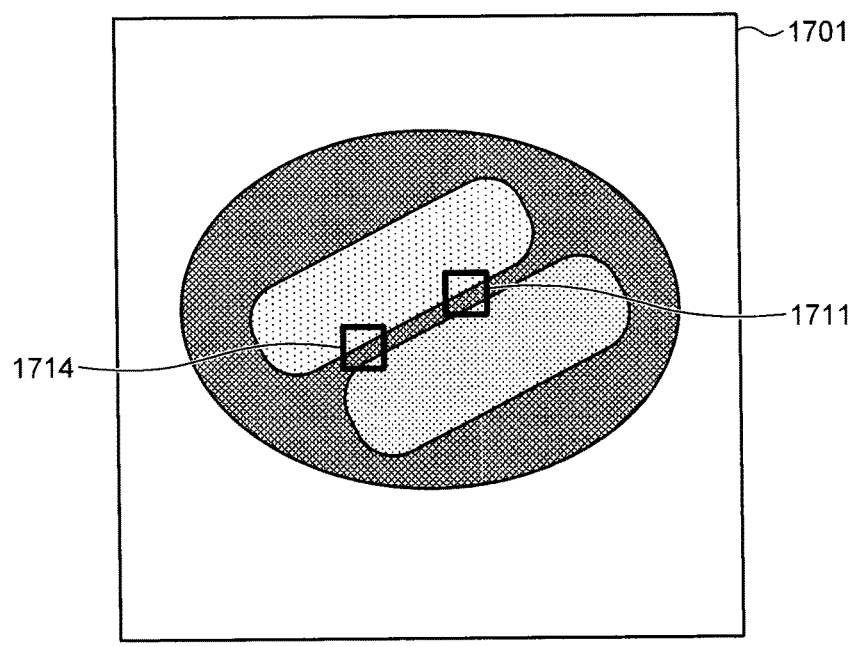
FIG. 30 is a diagram illustrating an example in which a parent block congruent with a child block is detected.

FIG. 28 is a diagram illustrating an exemplary child block in a reconstructed image. FIG. 29 is a diagram illustrating exemplary parent blocks set around a target child block. FIG. 30 is a diagram illustrating an example in which a parent block congruent with a child block is detected. Thus, explained below with reference to FIGS. 28 to 30 are the operations performed by the block pair detector 343 of the image processor 34 according to the third embodiment.

The reconstructed image 1701 generated by the second reconstructor 342 has only a small degree of variability in the pixel values. In FIG. 28, each substance having a different pixel value is illustrated with a different color shade. The block pair detector 343 divides the reconstructed image 1701 illustrated in FIG. 28 into child blocks (first blocks) segmented in a reticular pattern in an identical manner to FIG. 8.

Then, for each target child block 1711 that is the target child block for processing from among the divided child blocks, the block pair detector 343 searches for a parent block 1712 (a second block) that is equal in size to the concerned child block and that has a similar pattern of pixel values, that is, searches for a parent block 1712 that is congruent with the target child block 1711. Herein, as illustrated in FIG. 29, the block pair detector 343 sets a plurality of parent blocks 1712 in a predetermined area around the target child block 1711, and searches the parent blocks 1712 for the parent block 1712 that is congruent with the target child block 1711. Alternatively, in a predetermined area around the target child block 1711, the block pair detector 343 shifts the parent block 1712 having the same size as the target child block 1711 one pixel at a time and searches for the parent block 1712 that is congruent with the target child block 1711. However, the target child block 1711 itself is not included in the parent blocks 1712 to be searched. Herein, "congruent" is a concept not only implying a case in which the pattern of pixel values in two blocks are completely congruent with each other, but also implying a case in which the pattern of pixel values in two blocks may include a predetermined error in congruency.

Given below is the detailed explanation of the method by which the block pair detector 343 searches for the parent block 1712 that is congruent with the target child block 1711. As described above, since the target child block 1711 and the retrieved parent block 1712 are of the same size, the block pair detector 343 does not perform a reduction process, which is illustrated in FIG. 11 according to the first embodiment, with respect to the retrieved parent block 1712. Hence, using the unchanged pixel values of the parent block 1712 and the pixel values of the target child block 1711, the block pair detector 343 calculates the absolute value error according to Equation (1) given above or calculates the squared error according to Equation (2) given above.

The block pair detector 343 determines that, of a plurality of parent blocks 1712, the parent block 1712 having the smallest calculated error is congruent with the target child block 1711, and detects that particular parent block 1712 as a detected parent block 1714 illustrated in FIG. 30. In this way, for each child block constituting the reconstructed image 1701, the block pair detector 343 searches for the parent block that is congruent with the concerned child block, and detects that particular parent block as the detected parent block. Moreover, regarding the parent block 1712 having the smallest calculated error, if the error is not equal to or smaller than a threshold value, the block pair detector 343 determines that the target child block 1711 does not have any congruent parent block 1712 and thus does not perform subsequent operations. Therefore, it becomes possible to avoid unnecessary operations. As a result of performing such operations, as illustrated in FIG. 30, the block pair detector 343 detects, in the reconstructed image 1701, a block pair of the target child block 1711 and the detected parent block 1714 that is congruent with the target child block 1711. Then, the block pair detector 343 sends position information about the target child block 1711 and the detected parent block 1714, which is similar to the target child block 1711, to the image averaging processor 344.

Given below is the explanation of an averaging process performed by the image averaging processor 344 of the image processor 34 according to the third embodiment.

In the reconstructed image (equivalent to the reconstructed image 1101 illustrated in FIG. 6) received from the first reconstructor 341, the image averaging processor 344 identifies, in an identical manner to FIG. 17, a block pair of a child block (a third block) and a parent block (a fourth block) at the position corresponding to the position indicated by the position information about block pairs that is received from the block pair detector 343. Meanwhile, as described above, since the child block and the parent block are of the same size, the image averaging processor 344 does not perform a reduction process, which is explained in the first embodiment, with respect to the parent block in the reconstructed image received from the first reconstructor 341.

Then, using the pixel values of the pixels of the child block of the block pair and using the pixel values of the pixels of the parent block of the block pair, the image averaging processor 344 performs weighted averaging in an identical manner to Equation (3) given above. Subsequently, in the reconstructed image received from the first reconstructor 341, the image averaging processor 344 replaces the pixel values of the pixels in the child block with values that are calculated by performing weighted averaging according to Equation (3), and sets the substituted values as the new pixel values. As far as weighted averaging and replacing the pixel values is concerned, the image averaging processor 344 performs those operations at each position indicated by the position information about child blocks that is received from the block pair detector 343 (i.e., performs those operations for each child block of the reconstructed image received from the first reconstructor 341).

The reconstructed image that is reconstructed by the first reconstructor 341 at a specific energy has identical positions and shapes of substances to the reconstructed image 1701. Hence, also in the reconstructed image generated by the first reconstructor 341, a child block and the corresponding parent block become congruent with each other. Thus, while performing weighted averaging according to Equation (3) with respect to the child block, even if the parent block is used by the image averaging processor 344, the averaging of pixel values in each substance is maintained because the weighted averaging is performed for the pixels in the same substances. Thus, the variability in the pixel values of the reconstructed image, which is generated by the first reconstructor 341, goes on decreasing. Consequently, by repeatedly performing weighted averaging with respect to the child block using the parent block, the image averaging processor 344 generates a restored image in which the pixel values are correct linear attenuation coefficients of the substances. In such an averaging process performed by the image averaging processor 344, since reduction process is not performed with respect to the parent block, it is not possible to achieve the effect in which the low-frequency components of variability in the pixel values causing noise make a transition to high-frequency components. However, in the restored image, averaging of pixel values is not done across the boundaries among the substances. Instead, the pixel values are averaged on a substance-by-substance basis. Hence, the variability in the pixel values decreases, and the accuracy of reconstruction can be enhanced. Particularly, as in the case of the target child block 1711 illustrated in FIG. 30, if parallel boundaries of substances are present, a parent block having a different size but being similar is not present around the child block. For that reason, there are times when reduction in the variability due to weighted averaging is not achieved to a sufficient effect. However, as described above, if the parent blocks have the same size as the child block, then a parent block congruent with the child block is detected as illustrated in FIG. 30. As a result, the effect of reducing the variability can be achieved.

Meanwhile, the repetitive weighted averaging performed by the image averaging processor 344 with respect to the child block using the parent block can be ended after a predetermined number of repetitions. Alternatively, when the difference between the pixel values replaced in the previous instance with the values obtained by weighted averaging and the values obtained in the current instance by weighted averaging (i.e., the average value or the total value of the difference between all pixels of a reconstructed image) becomes equal to or smaller than a predetermined threshold value, the repetitive weighted averaging can be ended.

Regarding the operation in which the block pair detector 343 detects a congruent parent block having the same size as the child block and the image averaging processor 344 performs weighted averaging with respect to the child block using the congruent parent block, it is also possible to implement that operation in the second embodiment.

In the image processing performed by the image processor 34, it is assumed that a single parent block congruent with a child block is used in weighted averaging with respect to the child block. However, that is not the only possible case. Alternatively, the image averaging processor 344 can perform weighted averaging using all of the parent blocks 1712 (second blocks) that are identified by the block pair detector 343 in a predetermined area around the target child block 1711 (a first block) illustrated in FIG. 30. In that case, for example, of a plurality of parent blocks 1712, the parent blocks 1712 having a small error with respect to the target child block 1711 can be given a greater weight, while the parent blocks 1712 having a large error with respect to the target child block 1711 can be given a smaller weight. As a result of performing weighted averaging of a plurality of parent blocks with respect to the child block, the changes in the pixel values before and after weighted averaging become spatially continuous, thereby making it possible to reduce the occurrence of an unnatural artifact attributed to weighted averaging.

Meanwhile, apart from performing correction by means of weighted averaging, the image averaging processor according to the embodiments and the modification examples described above can also perform correction, for example, by means of filter processing using a Rank value filter such as a median filter or by replacing the pixel values with values based on the parent blocks. With such measures too, it becomes possible to reduce the noise.

Figure 31:
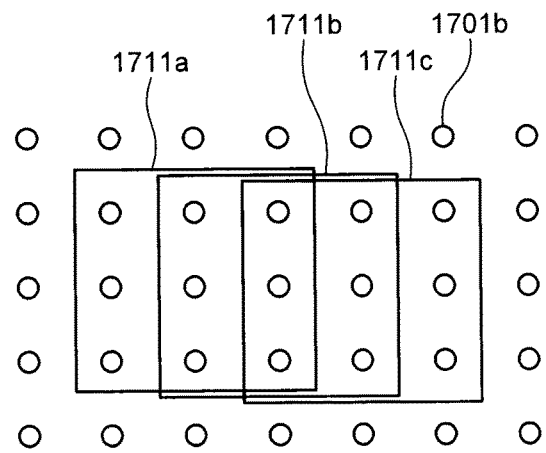
FIG. 31 is a diagram for explaining an operation in which a child block is shifted by one pixel at a time and processed.
Figure 32:
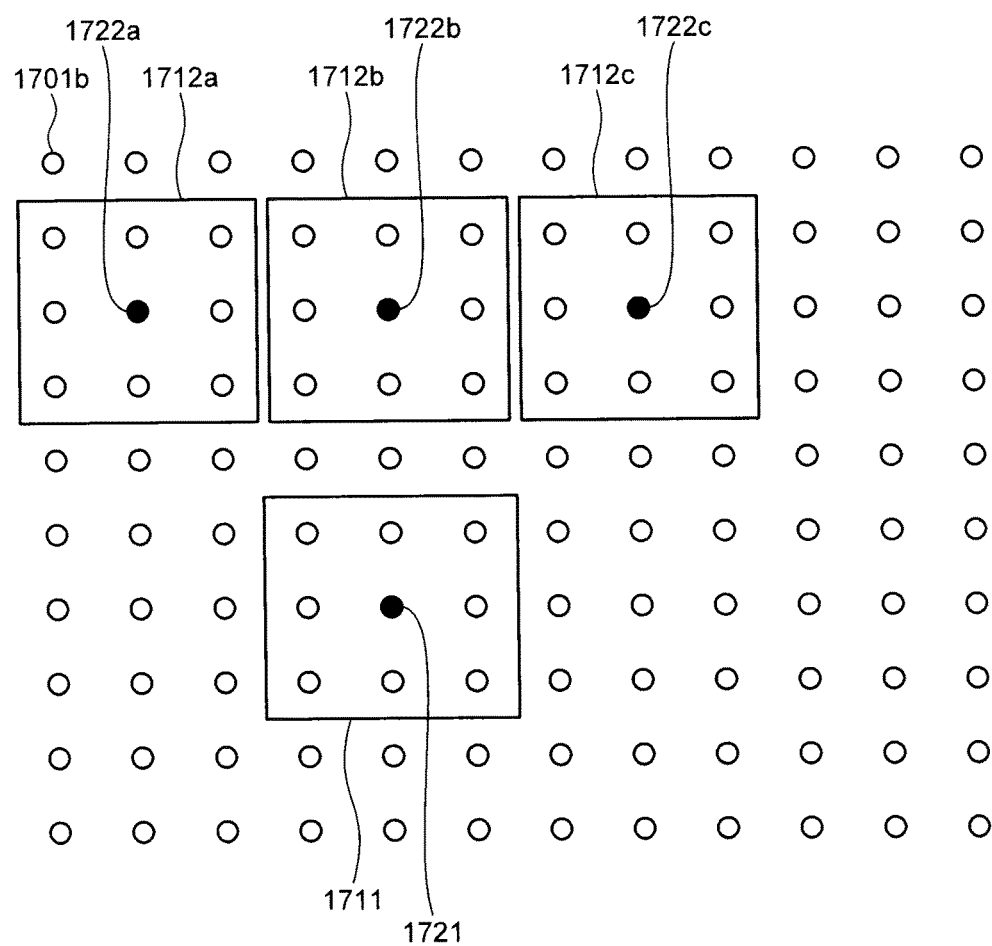
FIG. 32 is a diagram for explaining weighted averaging performed with respect to the central pixel value of a child block and central pixel values of parent blocks.

Moreover, in the image processing performed by the image processor 34, it is assumed that the block pair detector 343 divides the reconstructed image 1701 into child blocks segmented in a reticular pattern, and detects a congruent parent block for each of the divided child blocks. However, that is not the only possible case. That is, as the target child block 1711 that is the target child block for processing in the reconstructed image 1701, weighted averaging can be performed while shifting pixels 1701*b* constituting the reconstructed image 1701 one by one as in the case of target child blocks 1711*a* to 1711*c* illustrated in FIG. 31. In that case too, as described above, weighted averaging is performed using all of the parent blocks 1712 present in a predetermined area around the target child block 1711. Moreover, as illustrated in FIG. 32, the weighted average is calculated using the pixel in the reconstructed image (a first image), which is received from the first reconstructor 341, equivalent to a central pixel 1721 of the target child block 1711 and using the pixels in the reconstructed image, which is received from the first reconstructor 341, equivalent to central pixels 1722*a* to 1722*c* of a plurality of parent blocks (parent blocks 1712*a* to 1712*c*). As a result, it becomes possible to further reduce the occurrence of an unnatural artifact attributed to weighted averaging. Meanwhile, if the weighted averaging process (an averaging process) is to be implemented in the X-ray inspection device according to the second embodiment in which the averaging process and the reconstruction process using the successive approximation are performed in a simultaneous manner, pixel values g(i, j) of the image with respect to which the image averaging processor 343*c* performs weighted averaging are obtained according to, for example, Equation (7) given below.

$$g(i,j) = \frac{\sum_{n=-N}^{N}\sum_{m=-M}^{M}\left\{f(i+m,j+n)\exp\left(-\frac{\left(\frac{1}{4XY}\sum_{y=-Y}^{Y}\sum_{x=-X}^{N}\left[\begin{array}{c}r(i+x,j+y)-\\r(i+m+x,j+n+y)\end{array}\right]\right)^2}{2\sigma^2}\right)\right\}}{\sum_{n=-N}^{N}\sum_{m=-M}^{M}\left\{\exp\left(-\frac{\left(\frac{1}{4XY}\sum_{y=-Y}^{Y}\sum_{x=-X}^{N}\left[\begin{array}{c}r(i+x,j+y)-\\r(i+m+x,j+n+y)\end{array}\right]\right)^2}{2\sigma^2}\right)\right\}} \quad (7)$$

In Equation (7), (i, j) represents the position of a pixel in the temporary reconstructed image 1501. Moreover, f(i, j) represents the linear attenuation coefficient serving as the pixel value (the updated value) of the pixel at the position (i, j) in the temporary reconstructed image 1501. Furthermore, g(i, j) represents the pixel value of the pixel at the position (i, j) in an image obtained when the image averaging processor 343*c* performs weighted averaging with respect to the temporary reconstructed image 1501. Moreover, r(i, j) represents the pixel value of the pixel at the position (i, j) in the reconstructed image 1201 that is generated by the reconstructor 345*c* by reconstructing a subject sinogram after generating the subject sinogram from a spectrum, which is represented by the energy-by-energy photon count of the X-rays, and by adding the photon count of either a plurality of energies of the spectrum or all energies of the spectrum for each view and each channel. Furthermore, a represents an adjustment parameter switched according to the amount of noise. When the image averaging processor 343*c* performs weighted averaging with respect to the temporary reconstructed image 1501 using Equation (7), weighted averaging is performed using the pixel values of the parent blocks present within a range of (2M+1)×(2N+1) pixels centered on the position (i, j).

Figure 33:
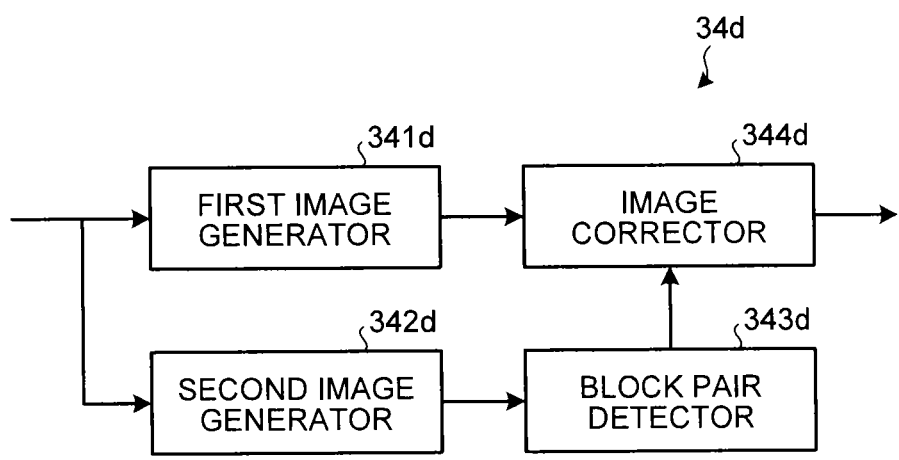
FIG. 33 is a diagram illustrating another exemplary block configuration of the image processing unit.

In the first and third embodiments, the explanation is given about the image processing performed in a CT scanner. However, the image processing is not limited to be performed in a CT scanner. Alternatively, for example, the image processing can be performed with respect to images taken by an MRI device (MRI stands for Magnetic Resonance Imaging). In an MRI device, various types of images are generated according to the purpose of diagnosis. For example, in an MRI device, a T1-weighted image is generated in the case of checking iron deposits and melanin; while a T2-weighted image is generated in the case of checking water and blood. FIG. 33 is a diagram illustrating another exemplary block configuration of the image processor. Explained below with reference to FIG. 33 is a case in which the image processing according to the first and third embodiments is implemented in a device (modality) other than a CT scanner. For example, the explanation is given for an example in which the modality is assumed to be an MRI device.

As illustrated in FIG. 33, an image processor 34*d* includes a first image generator 341*d*, a second image generator 342*d*, a block pair detector 343*d*, and an image corrector 344*d*.

The first image generator 341*d* generates a fat suppression image (a first image) as the diagnostic image. Herein, in a fat suppression image, fat signals are selectively lowered using a known technology such as inversion recovery or short TI inversion recovery (STIR). However, in a fat suppression image, noise can occur easily.

The second image generator 342*d* generates a T2-weighted image (a second image) that, for example, represents a reference image in which the same portion of the subject as captured in the fat suppression image is captured without suppression. Herein, as compared to the fat suppression image, the T2-weighted image has a different substance-by-substance average of pixel values and has a lower level of noise. Moreover, the T2-weighted image is a clearer image.

The block pair detector 343*d* is a processing unit that divides the T2-weighted image, which is received from the second image generator 342*d*, into child blocks (first blocks) and detects parent blocks (second blocks) each of which is similar to one of the child blocks. Then, the block pair detector 343*d* sends position information about pairs of child blocks and the respective similar parent blocks to the image corrector 344*d*.

The image corrector 344*d* is a processing unit that, in the fat suppression image received from the first image generator 341*d*, identifies a block pair at the position indicated by the position information about block pairs that is received from the block pair detector 343*d*; and performs correction in which the pixel values are replaced with values obtained by performing weighted averaging of the pixel values of the child block (a third block) in the identified block pair and the pixel values of a reduced block obtained by reducing the parent block (a fourth block) in the identified block pair. With respect to a child block, the image corrector 344d repeatedly performs weighted averaging using a reduced block obtained by reducing the parent block, and generates a restored image in which the pixel values correspond to each substance. As a result of repeated weighted averaging performed by the image corrector 344d, the pixel values in the restored image are corrected on a substance-by-substance basis. Hence, the variability in the pixel values decreases, and the accuracy of the pixel values of the fat suppression image, which represents the diagnostic image, can be enhanced. Herein, although the image corrector 344d performs correction by means of weighted averaging, that is not the only possible case. Alternatively, for example, it is needless to say that correction can be performed by means of filter processing using a Rank value filter such as a median filter or by replacing the pixel values with values based on the parent blocks.

Moreover, although the first image generator 341d generates a fat suppression image (a first image) as the diagnostic image, that is not the only possible case. Alternatively, for example, it is also possible to generate a water suppression image using a known technology such as fluid attenuated IR (FLAIR). In that case too, the noise in the water suppression image can be removed.

In this way, in the situation when noise occurs in a diagnostic image used in an MRI device, the diagnostic image can be generated by the first image generator 341d. Moreover, a different image having a lower level of noise can be generated as the reference image by the second image generator 342d. Then, a correction operation can be performed using the functions of the block pair detector 343d and the image corrector 344d. With that, it becomes possible to reduce the noise in the diagnostic image. Meanwhile, other than the example of the diagnostic image and the reference image given above, when the diagnostic image is a T1-weighted image or a T2-weighted image (a first image), the correction operation is effective also in the case in which the average image (a second image) of the T1-weighted image and the T2-weighted image or a proton image (a second image) is used as the reference image. When the diagnostic image is a diffusion-weighted image, the correction operation is effective also in the case in which a non-diffusion image (a second image) is used.

Meanwhile, the image processing described above can also be implemented when an ultrasonic diagnostic equipment is used as the modality. For example, the first image generator 341d generates, as the diagnostic image, a harmonic image (a first image) that represents an image of high-frequency components of ultrasonic waves. In a harmonic image, there is less multiple reflection in the vicinity of the body surface of the subject, and the artifact is also small. However, since there is a decline in sensitivity as compared to the fundamental harmonic, the noise occurs easily. The second image generator 342d generates, as the reference image, a B-mode image (a second image) of the fundamental harmonic by capturing the same portion that is captured in the harmonic image. Then, the block pair detector 343d and the image corrector 344d perform identical operations as described above. As a result, it becomes possible to reduce the noise in the harmonic image representing the diagnostic image. Moreover, in the case of diagnosing at a high frame rate, the beam count per frame decreases, thereby leading to a decline in the image quality. In that regard, if a low-frame-rate image having a large beam count (a second image) is used as the reference image, and if a high-frame-rate image having a small beam count (a first image) is used as the diagnostic image; then the image quality can be improved by performing the image processing using the image processor 34d.

Moreover, the image processing described above can also be implemented when an X-ray fluoroscope is used as the modality. In that case, in a roadmap display in which a difference image of a contrast image and a non-contrast image is superimposed on a perspective image; generally, a perspective image (a first image) obtained in a perspective mode in which generally the amount of X-rays is small and the noise is large is used as the diagnostic image, while a contrast image having a large amount of X-rays, or a non-contrast image having a large amount of X-rays, or an average image of those images (a second image) is used as the reference image. Then, the image processing is performed using the image processor 34d. As a result, it becomes possible to have a clear roadmap display of the perspective image representing the diagnostic image.

Meanwhile, when the same portion of the subject is captured also in a different modality and when an ultrasonic image (a first image) serves as the diagnostic image, a CT image or an MRI image can be used as the reference image. With that, the noise in the ultrasonic image serving as the diagnostic image can be reduced.

Moreover, when there is no deformation in the body part to be captured in the subject, performing the image processing using the image processor 34d is effective if data (a second image) obtained at a different timing than the timing of taking the diagnostic image (a first image) is used as the reference image.

In this way, with respect to various types of the diagnostic image (a first image), if the image processing using the image processor 34d is performed in which an image capturing the same body part under a different condition is treated as the reference image (a second image), it becomes possible to reduce the noise. Herein, regarding the different condition, whether the same modality is used or a different modality is used is no object.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing device, comprising: processing circuitry configured to
    generate a first image based on first data corresponding to photons with a first energy from among data that is obtained based on an energy of radiation that has passed through a subject bombarded with the radiation;
    generate a second image based on second data corresponding to photons with a second energy different from the first energy,
    find, in the second image, a second block having a similar pattern of pixel values to a first block included in the second image, the similar pattern being a pattern that is not a congruent pattern but a pattern that becomes a congruent pattern when resized,
    calculate, by using pixel values included in a third block in the first image that is positioned corresponding to a position of the first block in the second image and pixel values included in a fourth block in the first image that is positioned corresponding to a position of the second block in the second image, new pixel values corresponding to the third block, and perform a correction on the pixel values of the third block based on the new pixel values corresponding to the third block.

2. The device according to claim 1, wherein the first data represents a first count of the photons of the first energy, and the second data represents a second count of the photons of the second energy, the second count being greater than the first count.

3. The device according to claim 1, wherein the processing circuitry is further configured to generate, as the first image, a first sinogram from the first data corresponding to the photons with the first energy, generate, as the second image, a second sinogram from the second data corresponding to the photons with the second energy, and reconstruct an image on which the correction has been performed to generate a reconstructed image.

4. The device according to claim 1, wherein the processing circuitry is further configured to generate, as the first image, a first perspective image from the first data corresponding to the photons with the first energy, and generate, as the second image, a second perspective image from the second data corresponding to the photons with the second energy.

5. The device according to claim 1, wherein the processing circuitry is further configured to generate a subject sinogram from the second data corresponding to the photons with the second energy, and generate, as the second image, a reconstructed image by reconstruction based on the subject sinogram, perform the correction on a first temporary reconstructed image having temporary pixel values, generate a second temporary reconstructed image as the first image having pixel values updated by updated values that are calculated based on the first data corresponding to the photons with the first energy and based on pixel values of an image on which the correction has performed, and perform the correction on the second temporary reconstructed image.

6. The device according to claim 1, wherein the processing circuitry is further configured to find the second block, which is larger than the first block, and generate a reduced block by reducing the fourth block to a size of the third block, and perform weighted averaging using the pixel values of the third block and pixel values of the reduced block.

7. The device according to claim 1, wherein the processing circuitry is further configured to find, as the second block, a candidate block having a smallest error with respect to the first block from among candidate blocks serving as candidates for having the similar pattern of pixel values to the first block.

8. A radiation detecting device, comprising:

the image processing device according to claim 1;

a radiation tube configured to emit the radiation; and a radiation detector configured to detect the energy of the radiation emitted from the radiation tube that has passed through the subject.

9. An image processing method, comprising: generating a first image based on first data corresponding to photons with a first energy from among data that is obtained based on an energy of radiation that has passed through a subject bombarded with the radiation;

generating a second image based on second data corresponding to photons with a second energy different from the first energy;

finding, in the second image, a second block having a similar pattern of pixel values to a first block included in the second image, the similar pattern being a pattern that is not a congruent pattern but a pattern that becomes a congruent pattern when resized;

calculating, by using pixel values included in a third block in the first image that is positioned corresponding to a position of the first block in the second image and pixel values included in a fourth block in the first image that is positioned corresponding to a position of the second block in the second image, new pixel values corresponding to the third block; and performing a correction on pixel values of the third block based on the new pixel values corresponding to the third block.

* * * * *